(12) United States Patent
Yigzaw

(10) Patent No.: US 6,811,795 B2
(45) Date of Patent: Nov. 2, 2004

(54) ANTI-CANCER EXTRACTS AND PHARMACEUTICAL COMPOSITIONS AND METHODS

(76) Inventor: Tesfaye Zerihun Yigzaw, 8909 Drake Pkwy., Chattanooga, TN (US) 37416

( * ) Notice: Subject to any disclaimer, the term of this patent is extended or adjusted under 35 U.S.C. 154(b) by 24 days.

(21) Appl. No.: 09/442,256

(22) Filed: Nov. 17, 1999

(65) Prior Publication Data

US 2002/0004075 A1 Jan. 10, 2002

(51) Int. Cl.$^7$ .......................... A61K 35/78; A61K 9/48; A61K 9/20; A61K 9/14
(52) U.S. Cl. ...................... 424/725; 424/451; 424/464; 424/489; 424/774; 424/776; 424/778; 424/779
(58) Field of Search ................................. 424/725, 451, 424/464, 489, 774, 776, 778, 779

(56) References Cited

PUBLICATIONS

Computer Caba Abstract 2000:53058 Kavimani et al, 1999.*
Computer Biosis Abstract 1990:92285 Ageel et al 1989.*
Computer Scisearch Abstract 91:548657 Shah et al 1991.*

* cited by examiner

Primary Examiner—Herbert J. Lilling

(57) ABSTRACT

Compositions having therapeutic value derived from plant material from one or more of *Glinus lotoides, Ruta chalepensis, Hagenia abyssinica*, and/or *Millettia ferruginea* are provided. The compositions are useful in treating and preventing cancer and other diseases. Methods of preparing such compositions and methods for treating patients by administering the compositions, either alone or with a pharmaceutical carrier or excipient, are provided.

41 Claims, 32 Drawing Sheets

CAM - YIGN: PC - 3

| CAM - YIGN concentration (%) | Cell density (% of control) |
|---|---|
| 0 | 100 |
| 0.0004 | 82 |
| 0.0008 | 57 |
| 0.0016 | 57 |
| 0.0031 | 56 |
| 0.0062 | 49 |
| 0.0125 | 53 |
| 0.025 | 50 |
| 0.05 | 42 |
| 0.1 | 36 |

Figure 13

ANTI-CANCER EXTRACTS AND PHARMACEUTICAL COMPOSITIONS AND METHODS

BACKGROUND OF THE INVENTION

1. Field of the Invention

The present invention relates generally to the field of medicine and pharmacology. More particularly, the present invention relates to compositions having therapeutic value comprising extracts of plant material from one or more of *Glinus lotoides, Ruta chalepensis, Hagenia abyssinica* and *Millettia ferruginea*. The compositions of the present invention are useful in the treatment and prevention of cancer and other diseases. The present invention further relates to methods of preparing such compositions, and methods for the treatment and prevention of disease by administration of the compositions to a patient in need thereof.

2. Description of Related Art

Herbal medicine involves the application of plants or plant parts, without chemical processing, as therapeutic agents for the treatment of human disease. The practice of herbal medicine can be traced back to the most ancient cultures, with some remedies known for thousands of years, and remains the primary form of medicine practiced by many groups today. Much of modern pharmacology is based on herbal medicine, with plant-derived compounds accounting for one quarter of pharmaceuticals (Foster, S, Duke, JA, Eastern/Central Medicinal Plants (Peterson Field Guides), Boston, Houghton Mifflin (1990), vii.). Common plant-derived pharmaceuticals include, for example, digoxin (*Digitalis lanata*), oral contraceptives (progestin derived from *Diascorea villosa*) and cephalosporins (*Cephalosporium acermonium*).

In the last twenty years, there has been a resurgence of interest in herbal medicine (Fugh-Berman, A., Clinical Trials of Herbs, in Primary Care 24: Complementary and Alternative Therapies in Primary Care, 889–903 (John L. Randall and Joel S. Lazar, eds.,1997)); (Lozoya, X., Ciba Found Symp (1994) 185: 130–40). Much of this interest is attributable to a growing awareness that the diversity of the plant kingdom represents a vast (and potentially endangered) resource for the discovery of novel pharmaceuticals (Akerele, O., World Health Forum (1993) 14: 390–5). One study, for example, notes that the 119 drugs of known structure that are produced commercially from plants account for only 90 species of higher plants (Farnsworth, N., Ciba Found Symp (1990) 154: 2–11). With estimates of the total number of species in the world's flora ranging from 250,000 to 500,000 (and possibly greater), the possibilities are evident (Ayensu, E., Endangered Plants in the United States, Smithsonian Institution Press, 1978). The World Health Organization (WHO) has recognized this potential and made a significant policy commitment to encouraging the study of ethnobotany as a way to efficiently identify plants containing bioactive components.

Renewed interest in herbal medicine can also be attributed to another phenomena—a growth of interest in complementary or alternative medicine (Eisenberg, D. et al., JAMA (1998) 280: 1569–75). Studies suggest that between 30 and 50 percent of the adult population in industrialized nations use some form of complementary and/or alternative medicine to prevent or treat a wide variety of health problems (Astin, J. et al., Arch Inter Med (1998) 158: 2303–10). Herbal medicine is among the most popular forms of complementary or alternative medicine, and its popularity has risen in parallel to that of complementary or alternative medicine. One study indicates that more than one third of Americans use herbs for health purposes (O'Hara et al., Arch Fam Med (1998) 7: 523–36). Medicinal plants and plant products may be used in lieu of mainstream therapies, but are often used in conjunction with traditional remedies. Herbal medicine is perhaps even more popular in Europe, where patients have been active in demanding natural alternatives to synthetic drugs (Harrison, P., CMAJ (1998) 158: 637–9).

The increased demand for herbal medicine reflects the public's desire for more natural, effective or safer methods for treating disease. Widespread and increasing use of herbal remedies has been reported, for example, for inflammatory bowel disease (Rawsthorne, P. et al., Am J Gastroenterol (1999) 94: 1298–303); musculoskeletal disorders such as rheumatoid arthritis (Chandola, A. et al., J R Soc Med (1999) 92: 13–16; and HIV-related diseases (Ostrow, M. et al., J Acquire Immune Defic Syndr Human Retroviral (1997) 15: 115–20).

A variety of plants have been identified for their potential use as treatments for these diseases, among others. Plant extracts identified as potential HIV-inhibitors include, for example, Labiatae (Yamasaki, K. et al., Biol Pharm Bull (1998) 21: 29–33) *Prunella vulgari* (Yao, X. et al., Virology (1992) 187: 56–62); *Coptis chineusis, Ligusticum wallichii, Illicium lanceolatum, Isatis tinctoria, Lonicera japonica, Salvia miltiorrhiza, Eyrcibe obstusifolia, Acanthopanax graciliatylus, Bostaurus domesticus, Scutellaria baicaleusis,* and *Inula helenium* (U.S. Pat. No. 5,178,865). Chinese herbs, including Schizandrae, have proven beneficial in the treatment of chronic viral hepatitis (Sinclair, S., Altern Med Rev (1998) 3: 338–44).

Many herbal remedies are now being subject to clinical trials (Klepser, T. et al., Am J Health System Pharm (1999) 56: 125–38); (Fugh-Berman, A., Clinical Trials of Herbs, in Primary Care 24: Complementary and Alternative Therapies in Primary Care, 889–903 (John L. Randall and Joel S. Lazar, eds.,1997). Several medicinal plants have shown good results clinically, including *Hypercium performatum* (for depression); *Allium sativum* (hypercholesterolemia); *Emblica officinalis* (for hypercholesterolemia); *Tanacetum parthenium* (for migraines); *Ginkgo bilboa* (for dementia); *Artemisia annua* (for malaria and other parasites); *Zingiber officinale* (for nausea and emesis); and a variety of Chinese herbs (for HIV).

Perhaps nowhere is a greater desire for safer, more effective remedies seen than in the search for cancer treatments. An estimated 1.2 million new cases of invasive cancer will be diagnosed in the United States in 1999 (Landis, S. et al., CA Cancer J Clin (1999) 49: 8–31). Breast cancer alone will account for approximately 29% of these new cases. Plants and plant derived compounds have received attention as possible sources of novel therapeutics for cancer. Much of the work in this area is done under the auspices of the National Cancer Institute, which maintains an active screening program for medicinal plants (Cragg, G. et al., Ciba Found Symp (1994) 185: 178–90); (Cragg, G. et al., J Nat Prod (1993) 56: 1657–68). Plants and plant compositions identified as having potential for the treatment and/or prevention of cancer include extracts from the genus Geranium and Plantago and the species Calendula officinialis (PCT Application No. WO 98/24458); Peganum Harmala L. and Drakocephalum Kotshyi Boss. (PCT Application No. WO 99/24048); *Echinops spinosus* L. (PCT Application No. WO 99/24047); safflower extract (PCT Application No. WO 98/44005); *Portulaca oleracea* (PCT Application No. WO 98/24457); *Agaricus blazei* Murill (PCT Application WO 98/27992); *Solanum muricatum* (CSG) (Ren et al., Anticancer Res (1999) 19: 403–8); and *Beta vulgaris* (beet) (Kapadia et al., Cancer Lett (1996) 100: 211–4). Yet, the need for identification of suitable therapeutics remains high.

The present invention relates compositions and methods for the prevention and treatment of cancer and other diseases. The compositions of the present invention comprise extracts of plant material from *Glinus lotoides, Ruta chalepensis, Hagenia abyssinica*, and *Millettia ferruginea*, either alone or in combination. All four plants grow in the Waynadega region of Ethiopia where the rainfall is sufficient for vegetative growth. The use of at least several of these plants is known in indigenous cultures, though not in the form of the presently claimed composition nor for the claimed medicinal uses.

The plant *Glinus lotoides*, more commonly known as Mettre or, in Arabic, as Moghera, grows ubiquitously in the Allaqi area, south of Aswan, Egypt (Hamed et al., Phytochemistry (1996) 43: 183–188). Many species of the Glinus plant are eaten as green vegetables and possess a bitter flavor. Indigenously, *Glinus lotoides* serves a variety of medicinal purposes. It is used as an antiseptic, an anthelmintic, as a treatment for diarrhea and bilious attacks, and as a purgative for curing boils, wounds and pain in general. The juice of the plant is also sometimes given to weak children for strength (Hamed et al., Phytochemistry (1996) 43: 183–188). The use of *Glinus lotoides* to treat cancer has not yet been reported.

The plant *Ruta chalepensis*, also known as Tena Adam or rue, is a leafy, branched shrublet with an aromatic or pungent odor. The stems of the fully grown plants are two to three feet high. The leaves are compound (i.e., two or three times dissected) and are alternately arranged on the stems and branches. The yellowish-green flowers appear between February and May, followed by small, globular fruit. *Ruta chalepensis* is occasionally confused with *Ruta graveolens* (a distinct species) and vice versa. Key features known to distinguish *Ruta chalepensis* from *Ruta graveolens* include the shape of the leaves (elliptical vs. oblong), the margins of the petals (fringed vs. toothed), and the shape of the fruit lobes (pointed vs. rounded).

Medicinal uses of *Ruta chalepensis* are known, most often involving the aerial parts of the plant. In Saudi Arabia, for example, the aerial parts of the plant are used as a laxative, anti-inflammatory, antispasmodic, abortifacient, antiepileptic, emmenogogue, and to treat colic, headache, rheumatism, leucoderma and mental disorders (Shah et al., J Enthnopharmacol (1991) 34: 167–72); (Al-Said et al., J Ethnopharmacol (1990) 28: 305–312). In India, the plant is prescribed for dropsy, neuralgia, rheumatism, and menstrual and other bleeding disorders. The Chinese use a decoction of the roots as an antivenom and infuse the leaves with vinegar to treat children with convulsions and other nervous disorders. In Africa, an aqueous decoction of the leaves serves as a treatment for fevers. (Al-Said et al., J Ethnopharmacol (1990) 28: 305–312). Also of note, infusions of the leaves of the plant are know for use as stomach tonics, perspirants, and aborticides. *Ruta chalepensis* is also used, in combination with other herbs, in preparations for tooth and ear aches. The seeds of the plant, if taken with wine, have also been reported to provide an antidote for poisons. *Ruta chalepensis* is currently included on the FDA's GRAS (Generally Recognized as Safe) list (www.ars-grin.gov/duke/syllabus/gras.htm).

Researchers have conducted scientific studies of *Ruta chalepensis* to investigate the various medicinal applications of the plant and to evaluate the potential toxicity and genotoxic effect of extended use of the plant product (Shah et al., J Enthnopharmacol (1991) 34: 167–72). However, no studies have yet reported the use of *Ruta chalepensis* as a cancer treatment.

*Hagenia abyssinica*, commonly known as Kosso, grows at high altitudes and is indigenous to East Africa, particularly Ethiopia. It is known to use a decoction of the female flower of Kosso as an anthelmenic (e.g., to expel intestinal worms, such as Tapeworms). The female flower is preferred over the male flower due to the more intense and unpleasant emetic effect of the male flower. ((Woldemariam et al., J Pharm Biomed Anal (1990) 8: 859–65). It can be prepared as an unstrained tea by steeping the powdered flowers in distilled water for 15 minutes (Starlight Herbal).

Various scientific studies have been performed with *Hagenia abyssinica* to evaluate its use an anthelminic, to determine the chemical components of the plant (Woldemariam et al., J Pharm Biomed Anal (1990) 8: 859–65), and to investigate potential toxicity resulting from prolonged use (Arragie, M., Ethiop Med J (1983) 21: 89–93); (Shah et al., J Ethnopharmacol (1991) 34: 167–72). The use of *Hagenia abyssinica* as an anti-cancer agent has not been reported. The antitumor potential of kossins, the phloroguinol components of the plant which constitute 3% of the weight of the female flower, has been reported (Woldemarian, T. et al., J Pharm Biomed Anal (1992) 10: 555–60).

The medicinal use of *Millettia ferruginea*, and more particularly its use as an anti-cancer agent, has not been previously reported.

It is an object of the present invention to provide a composition comprising an extract of plant material from one or more of *Glinus lotoides, Hagenia abyssinica, Ruta chalepensis*, or *Millettia ferruginea* for the treatment or prevention of cancer and other diseases.

It is a further object of the present invention to provide a pharmaceutical composition for the treatment or prevention of cancer and other diseases, which composition comprises an extract of plant material from one or more of *Glinus lotoides, Hagenia abyssinica, Ruta chalepensis*, and *Millettia ferruginea* and a pharmaceutically acceptable carrier or excipient.

Another object of the present invention is to provide a method for making a composition comprising an extract of plant material from one or more of *Glinus lotoides, Hagenia abyssinica, Ruta chalepensis*, and *Millettia ferruginea* suitable for use in the treatment or prevention of cancer and other diseases.

Another object of the present invention is to provide a method for making a pharmaceutical composition comprising an extract of plant material from one or more of *Glinus lotoides, Hagenia abyssinica, Ruta chalepensis*, and *Millettia ferruginea* and a pharmaceutically acceptable carrier, suitable for use in the treatment or prevention of cancer and other diseases.

It is a further object of the present invention to provide a method for the prevention and treatment of cancer and other diseases by administration of the compositions or pharmaceutical compositions of the present invention.

Additional objects and advantages of the present invention are set forth herein, or would be readily apparent to one skilled in the art.

SUMMARY OF THE INVENTION

The present invention relates to compositions comprising extracts of plant material from *Hagenia abyssincia, Ruta*

*chalepensis, Millettia ferruginea,* or *Glinus lotoides,* either alone or in combination. The compositions of the present invention are useful in the treatment and prevention of cancer and other diseases. The compositions of the present invention include pharmaceutical compositions, comprising the extract or extracts in combination with a pharmaceutically acceptable carrier or excipient.

This invention also relates to a method for the preparation of the compositions of the present invention, including pharmaceutical compositions.

The present invention also relates to a method for preventing and or treating cancer or other diseases by the administration of the compositions of the present invention to a patient in need thereof. In particular, the present invention relates to a method of preventing or treating cancer, including breast cancer, prostate cancer, leukemia, melanoma and myeloma. The present invention further relates to a method of treating tuberculosis, diabetes, Parkinson's disease, and various fungal and viral infections, including HIV.

The compositions and methods of the present invention advantageously provide beneficial preventative and/or therapeutic effects while providing a natural option to patients seeking an complementary and/or alternative therapies for disease.

The invention will be described in detail by reference to the attached drawings and to specific embodiments thereof, neither of which should be viewed as limiting the invention or the appended claims.

BRIEF DESCRIPTION OF THE DRAWINGS

FIG. 13: represents a graph of the results of treating PC-3 cells with differing concentrations of a cell medium *Millettia ferruginea* extract (CAM-YING).

DETAILED DESCRIPTION OF SPECIFIC EMBODIMENTS

Figure 1A:
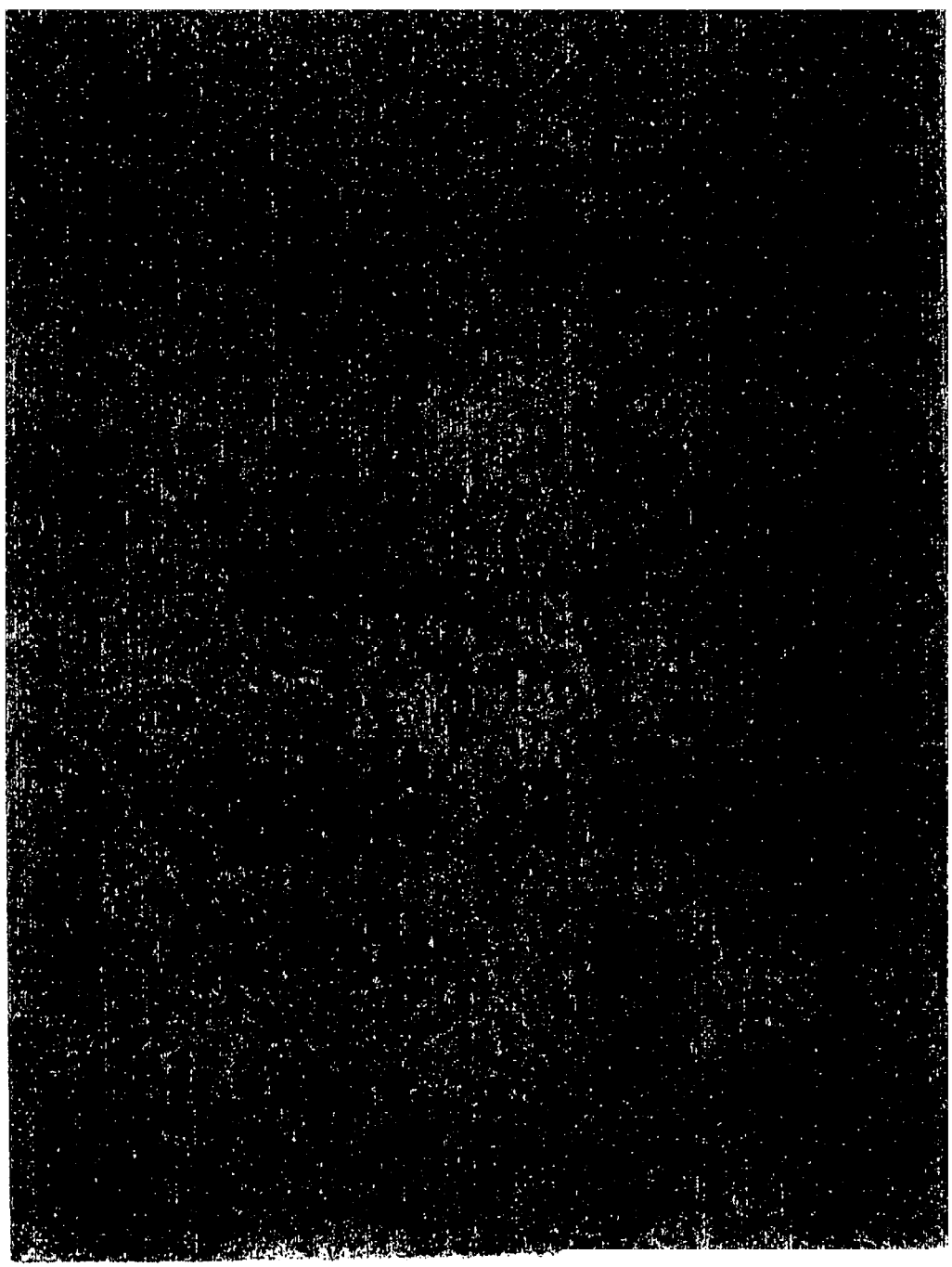
FIG. 1: depicts photomicrographs of MDA-435 cells treated with an organic solvent extract of *Hagenia abyssinica*. 1A represents the control. 1B represents a higher concentration (between 0.1–0.0125%) of *Hagenia abyssinica* extract. 1C represents a medium concentration (between 0.0062–0.0016%) of *Hagenia abyssinica* extract. 1D represents a lower concentration (between 0.0008–0.0004%) of *Hagenia abyssinica* extract.

The present invention relates to compositions suitable for the treatment or prevention of cancer and other diseases, as well as to methods of preparing and using these compositions.

The compositions of the present invention comprise one or more extracts of plant material from *Glinus lotoides, Ruta chalepensis, Hagenia abyssinica,* and *Millettia ferruginea,* either alone or in combination. A particular composition may comprise a single extract or may comprise two or more extracts in combination, of the same or different plant material. The plant extracts found in the compositions of the present invention are prepared from "plant material," a phrase intended to include any or all parts of the plant. Examples of suitable plant parts include, without limitation, seeds, flowers, leaves and stems. In a particular embodiment of the present invention, the plant material is dried.

The plant extract may be prepared from a single part of the plant, or from two or more parts of the plant. In a particular embodiment of the invention, the composition comprises an extract that is prepared from the dried seeds of *Ruta chalepensis, Millettia ferruginea*, or *Glinus lotoides*. In a further embodiment of the present invention, the composition comprises an extract that is prepared from the dried flowering parts of *Hagenia abyssinica*. In a more particular embodiment of the present invention, the composition comprises an extract that is prepared from both the dried flowering parts and the dried seeds of *Hagenia abyssinica*.

The compositions of the present invention may also contain, in addition to the plant extract or extracts, suitable pharmaceutical carriers or excipients. Suitable pharmaceutical carriers and excipients are reviewed in U.S. Pat. No. 5,952,374, the entire contents of which are incorporated herein by reference. The selection of suitable carriers or excipients is well within the skill of one trained in the pharmaceutical arts. In general, inert pharmaceutically acceptable carriers include starch, mannitol, calcium sulfate, magnesium stearate, dicalcium phosphate, silicic derivatives, and sugars (including, for example, sucrose, lactose and glucose). Binding agents include carboxymethyl cellulose and other cellulose derivatives, gelatin, natural and synthetic gums. Diluents typically include suitable oil, saline or sugar solutions. Other excipients include lubricants, disintegrating agents and adsorptive carriers, all of which are well known in the art. Coloring or flavoring agents may also be added to the composition of the present invention.

The pharmaceutical compositions of the present invention may be in the form, for example, of tablets, capsules, powders, suppositories, suspensions and solutions. Methods for producing these various pharmaceutical formulations are within the ability of one skilled in the art.

The compositions of the present invention which do not comprise pharmaceutical carriers or excipients may be in the form, for example, of liquids, powders or tablets. The most basic form of the composition of the present invention is the liquid product of the extraction process.

The compositions of the present invention contain at least a therapeutically effective amount of the plant extract. The therapeutically effective amount is considered to be that amount of the extract, in weight percent of the composition, which must be present in order to produce the desired therapeutic effect. As would be apparent to one skilled in the art, the therapeutically effective amount may vary, depending upon, for example, the disease to be treated and the form of administration. In general, the extract will be present in an amount ranging from about 1 to about 100% by weight of the composition. More particularly, the extract will be present in an amount ranging from about 10 to about 90% by weight, and even more particularly, from about 20 to about 80% by weight, and even more particularly, from about 30 to about 70% by weight, and even more particularly, from about 40 to about 60% by weight, and even more particularly, about 50% by weight of the composition.

The present invention also relates to a method of preparing the composition of the present invention, which method comprises extraction of plant material from one or more of *Glinus lotoides, Ruta chalepensis, Hagenia abyssinica* and/or *Millettia ferruginea*. The extraction should be performed under sterile conditions, to the extent possible. It is understood that the temperature may vary, though in general may range from about 4 to about 30° C. In a particular embodiment of the present invention, the plant material is dried. In a more particular embodiment, the dried plant material is reduced in overall size prior to extraction, for example by grinding, pulverizing or crushing the plant material to form a powder, thereby increasing the overall surface area available for extraction.

The method of the present invention can be carried out using one or more suitable extractants/solvents or mixtures thereof. Examples of suitable extractants include, without limitation, polar and non-polar organic solvents, cell media, and water.

In a particular embodiment of the present invention, the extraction is performed using cell media or water as the solvent/extract. Examples of suitable cell media extractants include, without limitation, 10% serum DMEM, serumless DMEM, RPMI 1640, HAM's F12, CMRL 1066, McCoy's 5A, Medium 199, Waymouth's MB752, Eagle's or Joklik's MEM, αMEM. The cell medium must be prepared under sterile conditions. The method of the present invention comprises providing a sample of plant material, which is optionally placed in a suitable container (i.e., a glass tube). The plant material is then contacted with the extractant (i.e., cell media or water) for a suitable period of time, resulting in extraction of the plant material and production of a liquid extract. In general, longer contact times are more desirable. The mixture of the plant material and the extractant is optionally agitated (i.e., by vortexing) to promote extraction. The mixture is then processed to separate the liquid extract from the crude material. Any suitable form of separation may be employed, including, but not limited to, filtration or separation by gravity. The extract is then collected. It may be desirable to perform the separation more than one time, in order to more completely separate the extract from the crude material. Optionally, the liquid extract is further processed, for example, by drying to produce a solid or powdered form.

In a particular embodiment of the present invention, a sample of plant material is weighed and placed in a glass tube. The cell media extractant is then added to the glass tube in an amount suitable to cover the plant material. The mixture of the plant material and the extractant is then vortexed vigorously for about a suitable time (i.e., from about 10 minutes to about 2 hours). In general, longer vortexing times are more desirable. After vortexing, the mixture is placed in an agitator in a cool room for a suitable time (i.e., from about 24 to about 48 hours). The mixture is then processed to separate the extract from the crude material. More particularly, the mixture is centrifuged one or more times for about a suitable time (i.e., from about 5 to about 10 minutes) at a suitable speed (i.e., from about 5000 to about 10,000 rmp) with the supernatant recovered each time, until almost no precipitate is formed upon centrifugation. The combined collected supernatants provide the liquid extraction product. The extract may be further processed, for example by drying to produce a solid or powdered form.

The extract of the present invention may also be prepared by extraction with a suitable organic solvent or a mixture of suitable organic solvents. Organic solvents suitable for use in the present invention include both polar and non-polar organic solvents, as would be familiar to one skilled in the art. Examples of suitable organic solvents include, without limitation, methanol, hexane, ether, or acetone. In a particular embodiment of the present invention, plant material from *Ruta chalapensis* is extracted with methanol, acetone or hexane. In a further embodiment of the present invention, plant material from *Millettia ferruginea* is extracted with hexane or acetone. In a still further embodiment of the present invention, plant material from *Hagenia absysinnica* is extracted with acetone or methanol.

In the organic solvent extraction, a sample of plant material is provided and contacted with a quantity of organic solvent. The extraction may be facilitated by providing the plant material in a suitable container (i.e., a glass tube). The plant material is contacted with the organic solvent or mixture of organic solvents for a suitable time, resulting in extraction of the plant material and production of a liquid extract. Optionally, the mixture of the plant material and the organic solvent or solvents is stirred or mixed to promote extraction. The mixture is then processed to separate the liquid extract from the crude material. Any suitable form of separation may be employed, including, but not limited to filtration. The extract is then collected.

Optionally, the crude material produced by the extraction is re-extracted. Further extractions may involve the use of the same organic solvent or mixture of organic solvents as the first extraction, or one or more different organic solvents or organic solvent mixtures. Extraction conditions may be varied during subsequent extractions, including, without limitation, altering the pH. The liquid extraction products of one or more extractions may then be combined.

In a particular embodiment of the particular invention, a sample of plant material is weighed and placed in a glass tube. A quantity of organic solvent is then added to the glass tube, in a volume sufficient to cover the plant material (i.e., an amount equal to approximately three times the plant material). After mixing for a suitable time (i.e., 3 to 6 days) to promote extraction, the solution is filtered to separate the extract (the filtrate) from the crude material (the filter cake). The liquid extract is set aside. The crude material produced during the first extraction is then optionally re-extracted with an additional volume of solvent (either the same solvent or mixture of solvents used in the first extraction, or a different solvent or a mixture of solvents), and adjusted to a pH from about 9 to about 13 (i.e., by the addition of NaOH). The mixture of the crude material and the additional solvent is then mixed or stirred, to promote extraction. After mixing for a suitable time (i.e., two to three hours) the solution is filtered to separate the extract from the crude material. This second extract is set aside, while the remaining crude material is optionally re-extracted with an additional volume of solvent (either the same solvent or mixture of solvents used in the second extraction, or a different solvent or mixture of solvents), and adjusted to a pH of from about 1 to about 5 (i.e., by the addition of HCL, <1M with a pH of about 1), then stirred for an additional period (i.e., from about 2 to about 3 hours) to promote further extraction. This mixture is then filtered to separate the extract from the crude material. Optionally, additional extractions are performed, using the same or different solvents or mixtures of solvents. Optionally, the liquid extracts of one or more extractions may be combined, to provide a single liquid extract.

In a more particular embodiment of the present invention, the first extraction of a sample of plant material is carried out with methanol, producing a liquid extract and crude material (i.e., a filter cake where filtration is employed). This first extraction is followed by a second extraction of the crude material produced during the first extraction, with acetone substituted for methanol as the extractant. The liquid extract produced by the acetone extraction is then combined with the liquid extract produced by the methanol extraction.

In a particular embodiment of the present invention, organic solvent extracts of a single sample of plant material are combined to produce a liquid extract (i.e., as described above in the context of a first methanol extraction, followed by a re-extraction of the crude material with acetone, and the combination of the two liquid extraction products). In a further embodiment of the present invention, organic solvent extracts of two or more samples of plant material are combined to produce a liquid extract. For example, a methanol extraction is carried out on a given sample of plant material, producing a liquid extract and crude material. The liquid extract is set aside, while the crude material is optionally discarded. A second plant sample is then extracted with methanol or a different organic solvent, and the liquid extract product of that second plant sample is combined with the liquid extract product of the first plant sample. Put another way, liquid extracts produced according to the present method represent both combinations of serial extractions of a single plant sample (i.e, a single sample of *Ruta chalepensis*), as well as combinations of single (or serial) extractions of two or more plant samples (i.e., two or more samples of *Ruta chalepensis*). In a particular embodiment of the present method, the liquid extract produced represents a combination of the liquid extracts produced by a single (or serial) extraction of two or more plant samples derived from different plants (i.e., a single plant sample derived from *Hagenia abyssinica* and a single plant sample derived from *Ruta chalepensis*).

Further processing of the liquid extraction product of *Millettia ferugginea* may be necessary, in order to remove oil that may be formed during the extraction process.

This liquid product of the organic solvent extraction or extractions can then be further processed to remove the organic solvent. In a particular embodiment of the present invention, the liquid product is dried by vacuum or vacuum distillation to produce a dried pellet product. In a further embodiment, the liquid product is centrifuged for about 5 to about 10 minutes at from about 10,000 to about 15,000 rpm. The liquid fraction (the solvent) is discarded, while the pellet is collected, washed in Diwater at least twice (to remove the solvent). The washed pellet is then air dried under a vacuum. In a particular embodiment of the present invention, the dried extraction product is resuspended in a suitable solution. The pH of the suspension may need to be adjusted, as well, to a value from about 6 to about 8, and more particularly, from about 7.1 to about 7.4, and even more particularly, to about 7.1.

The present invention further relates to methods of making the pharmaceutical compositions of the present invention. The liquid extraction product of either the cell medium or organic solvent extraction, or the dried product produced therefrom, can be further combined with one or more suitable pharmaceutical carrier or excipients to form the pharmaceutical compositions of the present invention. Suitable pharmaceutical carriers and excipients, as well as methods and conditions for producing pharmaceutical formulations, would be obvious to one skilled in the art, and need not be elaborated further herein. In general, suitable formulations include tablets, powders, capsules, suspensions, suppositories and solutions.

The present invention also relates to methods of preventing or treating cancer or other diseases by administration of the compositions of the present invention to a human being in need thereof. The compositions of the present invention have therapeutic value for the treatment of several types of cancer, including but not limited to, breast cancer, prostate cancer, leukemia, melanoma and myeloma. The compositions of the present invention also have therapeutic value for the treatment of viral infections, including HIV, diabetes, Parkinson's disease, tuberculosis, and fungal infections.

The compositions of the present invention comprise one or more extracts, including compositions comprising one or more extracts in combination with pharmaceutical carriers or excipients. Put another way, the liquid extraction product, or the dried version thereof, can be administered alone or in combination with one or more suitable pharmaceutical carriers or excipients.

The compositions of the present invention can be administered via any number of routes, including but not limited to, orally, intranasally, rectally, or parenterally. More particularly, suitable forms of parenteral administration include, but are not limited to, intravenous, subcutaneous, intramuscular and intraperitoneal injection.

As would be apparent to one skilled in the art, the proper dosage for administration to a patient will depend upon the disease treated, the form of administration, the disease state and the patient's particular characteristics (i.e., age and gender). Patients should consult their physicians with respect to the dose most suitable for their particular needs. In general, an acceptable and effective oral daily dose of the extract of *Millettia ferruginea* is from about 10 mg/kg to about 100 mg/kg, while the generally acceptable and effective intravenous daily dose is from about 5 mg/kg to about 20 mg/kg. In general, an acceptable and effective oral daily dose of the extract of Hygenia abyssinica is from about 50 mg/kg to about 200 mg/kg, while the generally acceptable and effective intravenous daily dose is from about 10 mg/kg to about 50 mg/kg. A generally acceptable and effective oral dose of *Ruta chalepensis* ranges from about 10 mg/kg to about 2 g/kg, while the generally acceptable and effective intravenous daily dose ranges from about 50 mg/kg to about 1000 mg/kg. The generally acceptable and effective oral dose of *Glinus lotoides* ranges from about 50 mg/kg to about 200 mg/kg, while the generally acceptable and effective intravenous daily dose ranges from about 10 mg/kg to about 50 mg/kg.

While the invention will be described in the examples below in relation to certain preferred embodiments, it should be understood that it is not intended to restrict the invention to these particular embodiments but is intended to include all alternatives, modifications and equivalents that fall within the scope of the appended claims.

EXAMPLE 1
Extraction of Plants with Non-Serum DMEM

Natural products, CAM-MsWM, CAM-ANQZ, CAM-YING, and MsWM-CAMY3T, were individually extracted from plants *Hagenia abyssinica* (Kosso), *Ruta chalepensis* (Tena Adam), *Millettia ferruginea* (Brebra), and *Glinus lotoides* (Mettere), respectively. Every attempt was made to perform the extraction under sterile conditions.

Dried plant samples of *Hagenia abyssinica, Ruta chalepensis* and *Glinus lotoides* were obtained from an Ethiopian marketplace, while *Millettia ferruginea* samples were collected in Ethiopia and then dried. Dried seeds were the form of plant material used for *Ruta chalepensis, Millettia ferruginea* and *Glinus lotoides*, while dried flowering parts were used for *Hagenia abyssinica*. It should be noted, however, that some small seeds were present in the dried flowering *Hagenia abyssinica* sample. In each case, a dried plant sample was placed in a glass tube with sufficient/ appropriate DMEM, covered, and vortexed for 10 to 20 minutes. The mixture was then placed on an agitator in a standard cool room for approximately 24 hours. After agitating, the mixture was then vortexed well, for about 10 to 20 minutes. The mixture was then centrifuged approximately 5 minutes at 6000 rpm, to produce a supernatant and a precipitate/pellet. The supernatant was collected and transferred to another glass tube. This glass tube was then centrifuged for 5 minutes at 6000 rpm to produce a supernatant and a precipitate/pellet. The supernatant was collected, and the centrifugation step repeated several times until no unsettled precipitate was observed. The final product of the extraction was supernatant, which provided a 0.1% cell media extract serving as a stock solution for testing on cancer cell lines, as detailed herein.

EXAMPLE 2
Extraction of Plants with Solvents

Natural products, CAM-MsWM, CAM-ANQZ, were individually extracted from plants *Hagenia abyssinica* (Kosso)and *Ruta chalepensis* (Tena Adam), respectively. The extraction process was performed under sterile conditions, to the extent possible.

Plant material from *Hagenia abyssinica* and *Ruta chalepensis* was obtained as described in Example 1. A dried sample was placed in a covered flask with enough methanol to cover the product in approximately a 3 to 1 ratio of methanol to product. This was then mixed with a stirrer in a standard cool room for 3 to 6 days. After mixing, the solution was filtered, producing a filter cake and a liquid filtrate. The filtrate was set aside. The filter cake was then placed in a flask with enough methanol to cover and enough NaOH (5M) to bring the mixture to a pH of 10. This mixture was stirred for 2–3 hours. The solution was then filtered to produce a filter cake and a liquid filtrate. The liquid filtrate was set aside. The filter cake was then placed into a flask with enough methanol to cover it. HCL (<1M, with a pH of about 1) was then added, and the solution was stirred for 2–3 hours. The solution was filtered, producing a filter cake and a liquid filtrate, which were both set aside.

The three liquid filtrate samples produced in the preceding steps were combined. The combined liquid sample was then centrifuged on high speed, 10,000 rpm for 5 minutes, to produce a supernatant and a precipitate. The precipitate was collected and set aside, while the supernatant was centrifuged at high speed several times, each time collecting the precipitate, until the supernatant produced was clear. The supernatant was then discarded, and the collected precipitate was washed and then dried. The dried precipitate was the product of the extraction process. The dried precipitate was then re-suspended in serumless DMEM, with a pH of 7.1. The resulting resuspended solution provided 0.1% extract suitable for use as a stock solution as detailed herein.

The filter cake produced during the preceding steps was then extracted according to the steps detailed above, although acetone was substituted for methanol, producing the 0.1% extract suitable for use as a stock solution as detailed herein.

A portion of this acetone extract of MsWM was then combined with a portion of the methanol extract of MsWM, providing the organic solvent extract mixture suitable for a stock solution as detailed.

EXAMPLE 3
Preparing Cancer Cell Lines

Four different human cancer cell lines were used. These included breast cancer cell lines (11–9–1–4, MDA-435 and MCF-7 ); a Myeloma cancer cell line (B16 F-1); and prostate cancer cell line (PC-3). Each cell line was grown at 37° C. in 10% Serum DMEM medium, except for the PC-3 line, which was grown in RPMI 1640 Media (MDA 321). The cells were grown until confluent and then washed once with PBS and aspirated. The cells were then washed in Trypsin, 10% serum DMEM was added, and the cell solution was aspirated in the test tube and centrifuged for 5 minutes at 6000 rpm. After centrifugation, the supernatant was discarded and the pellet was resuspended in two mls of 10% serum DMEM. 0.5 mls of this solution was combined with 15 mls of 10% serum DMEM and placed in a cell culture tube. The cells were counted by placing 20 μls of the cell suspension in a Hemocytometer, diluting as necessary for calculation.

The cell concentration was kept at approximately ten thousand per μl for testing against the extracted compounds.

EXAMPLE 4
Cytotoxicity of CAM-MsWM

CAM-MsMW, the 0.1% plant extract prepared as described in Examples 1 and 2, was serially diluted for testing on cancer cells at different concentrations. 300 μls of CAM-MsMW was diluted with 300 μls of 10% serum DMEM (1:1 extract to serum). The serial dilution was continued by sequential addition to test tubes containing 300 μls of 10% serum DMEM (with Media RPMI 1640 was substituted for the 10% serum DMEM in the experiments performed with the PC-3 cancer cell line). In each well of the test plate 150 μls of extract dilution was mixed with 20 μls of diluted cancer cells and incubated at 37° C. for 3–4 days. Cancer cell lines treated with CAM-MsWM include MDA-435 (breast), B16F1 (myeloma), MCF-7 (breast) and PC3 (prostate).

Figure 1B:
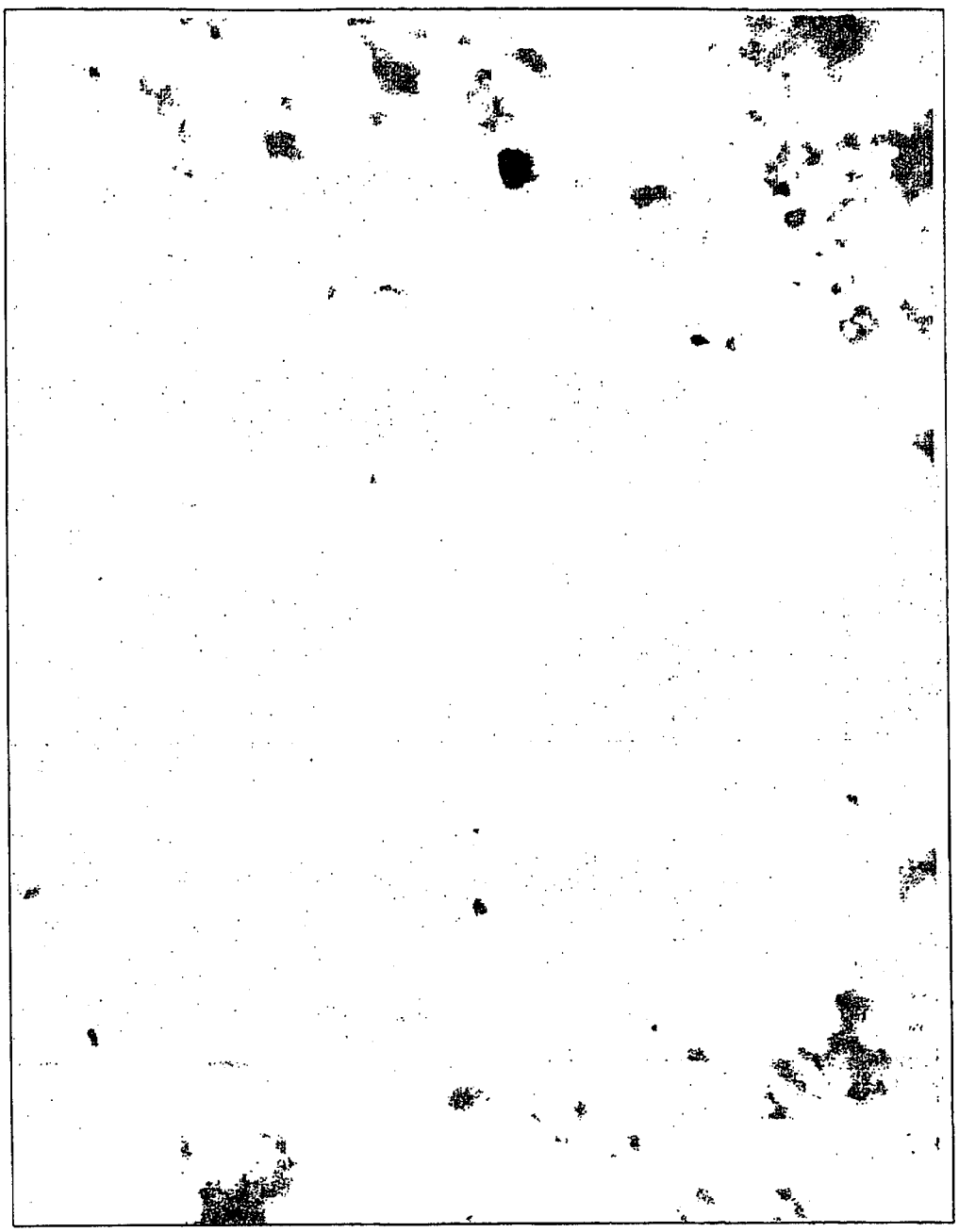
Figure 1C:
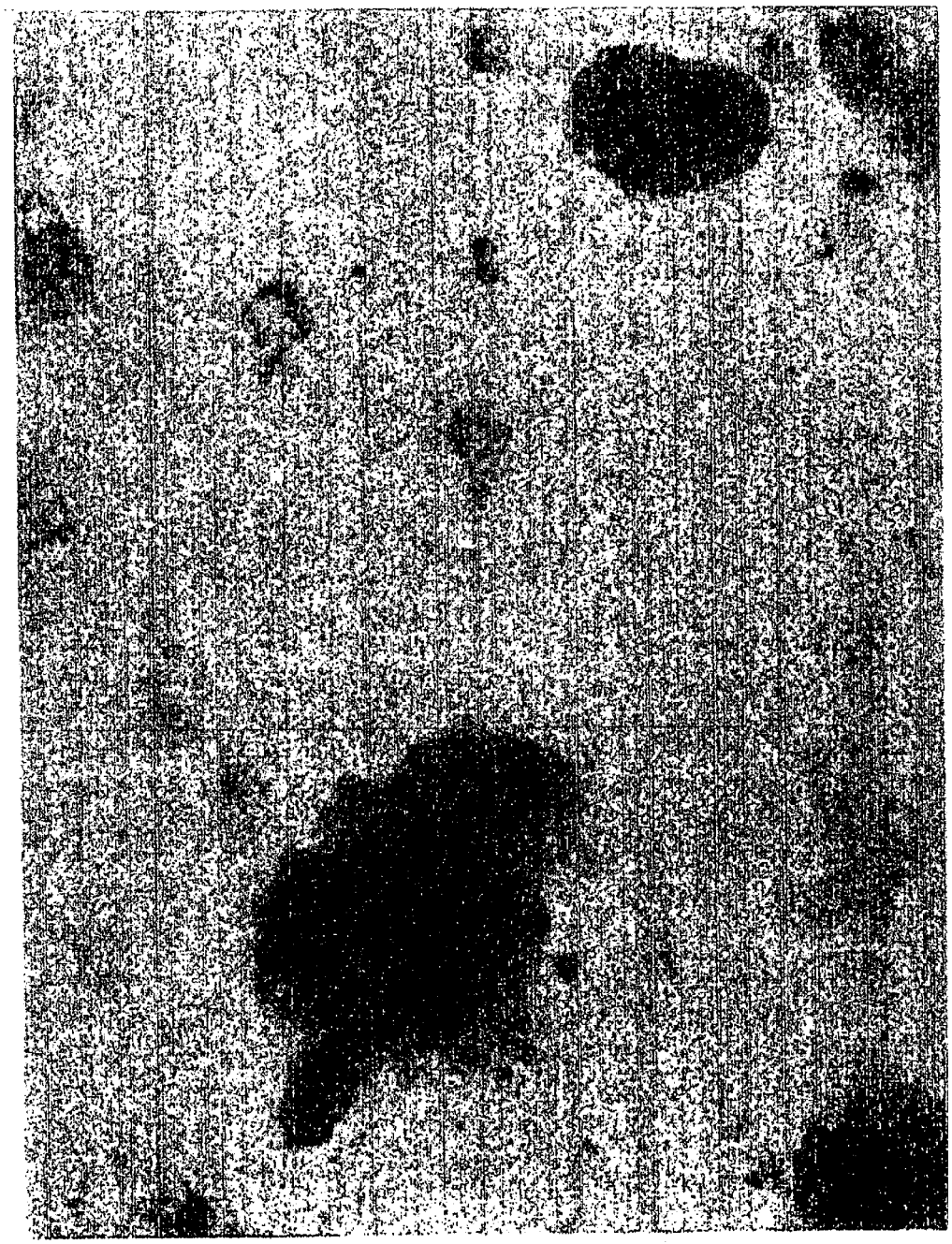
Figure 1D:
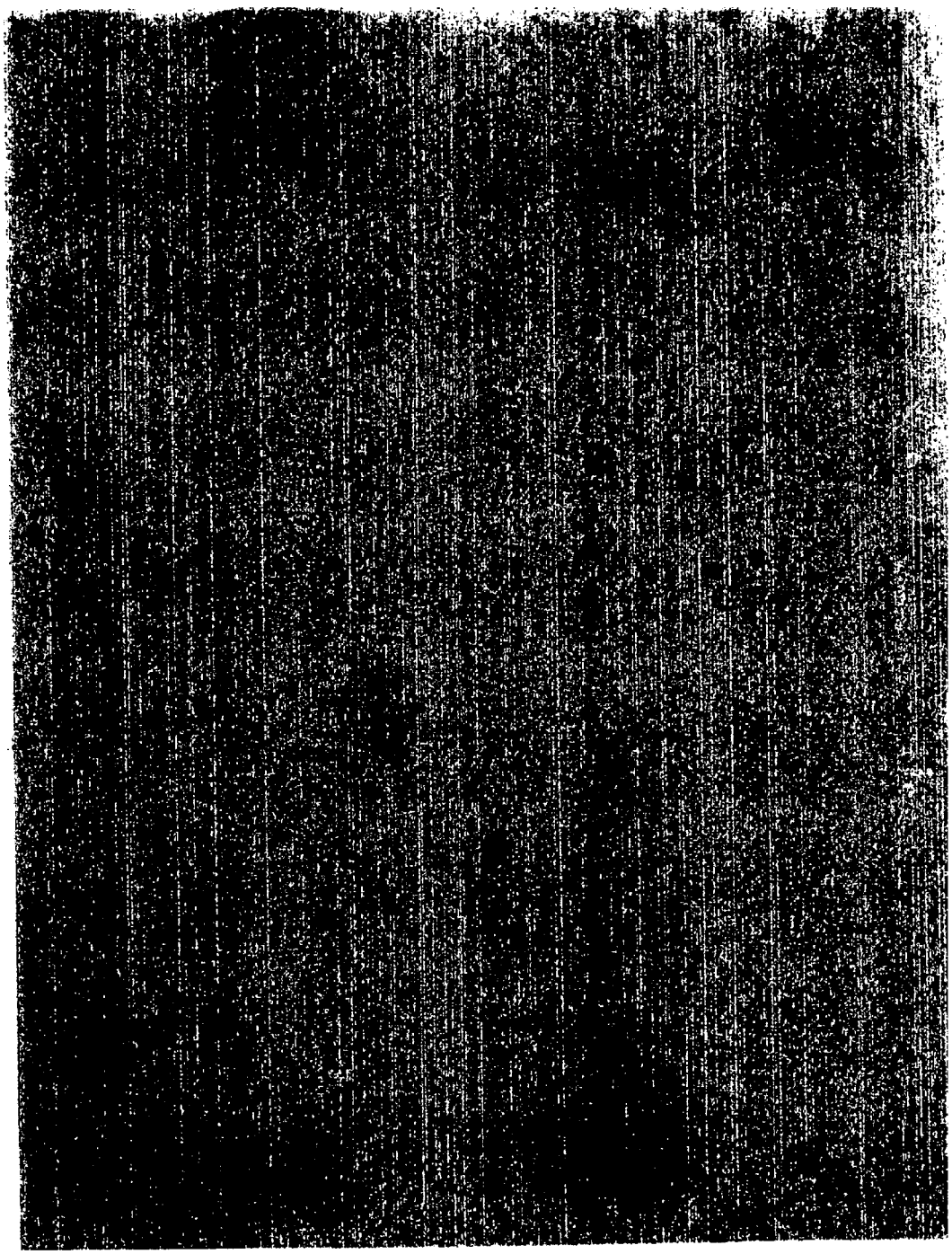

During this period, the cytotoxicity of the extracts was observed by examination under the microscope. FIG. 1 represents microscopic photographs of the effect of an organic solvent extract (CAM-MsMW) of *Hagenia abysinnica* on the MDA-435 cell line. FIG. 1A represents the control, while FIG. 1B shows the effect of a higher concentration (0.1–0.0125%) of CAM-MsWM. FIG. 1C show the cytotoxicity of a medium concentration (0.0062–0.0016%) of CAM-MsWM on these cells, while FIG. 1D depicts the cytotoxicity of a lower concentration (0.0008–0.0004%) of CAM-MsWM. The photomicrographs in FIG. 1 demonstrate that the toxicity of an organic solvent extract of CAM-MsWM for the MDA-435 cells appears to decrease with the concentration tested.

Figure 8:
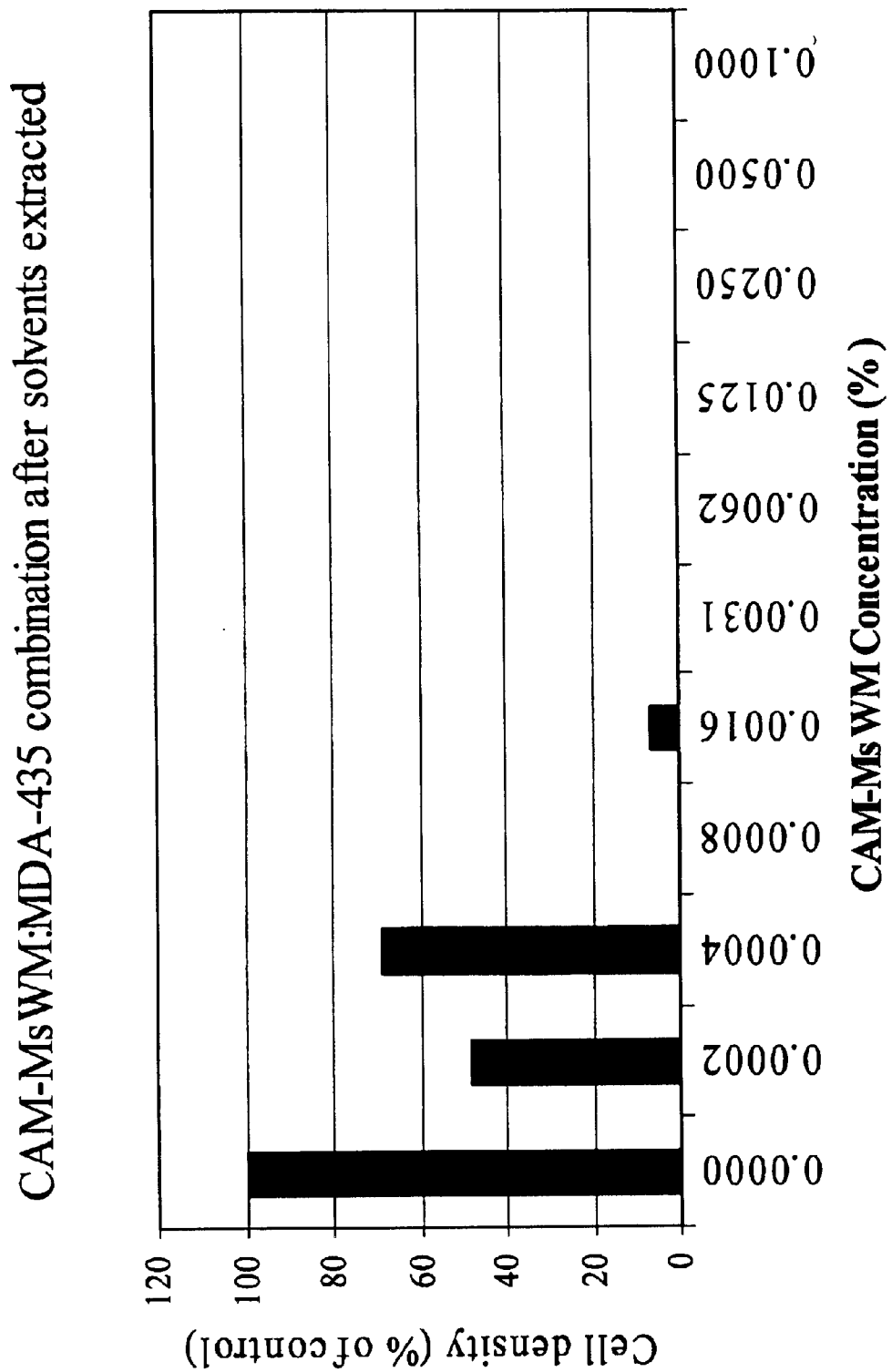
FIG. 8: represents a graph of the results obtained by treating MDA-435 cells with differing concentrations of a mixture of a methanol extract of *Hagenia abyssinica* and an acetone extract of *Hagenia abyssinica* (CAM-MsWM).

Cytotoxity was also evaluated by DYNE MRX. To accomplish this, 20 μls of Almarblue was added to each well of the test plate, incubating at 37° C. for at least four hours, and reading the oxidation level by DYNE MRX. FIG. 8 represents the effects of a combination of methanol and acetone extracts CAM-MsWM on the MDA-435 cells. The graph indicates that the mixture is highly toxic to cancer cells at high concentrations (above 0.0004%).

Figure 2:
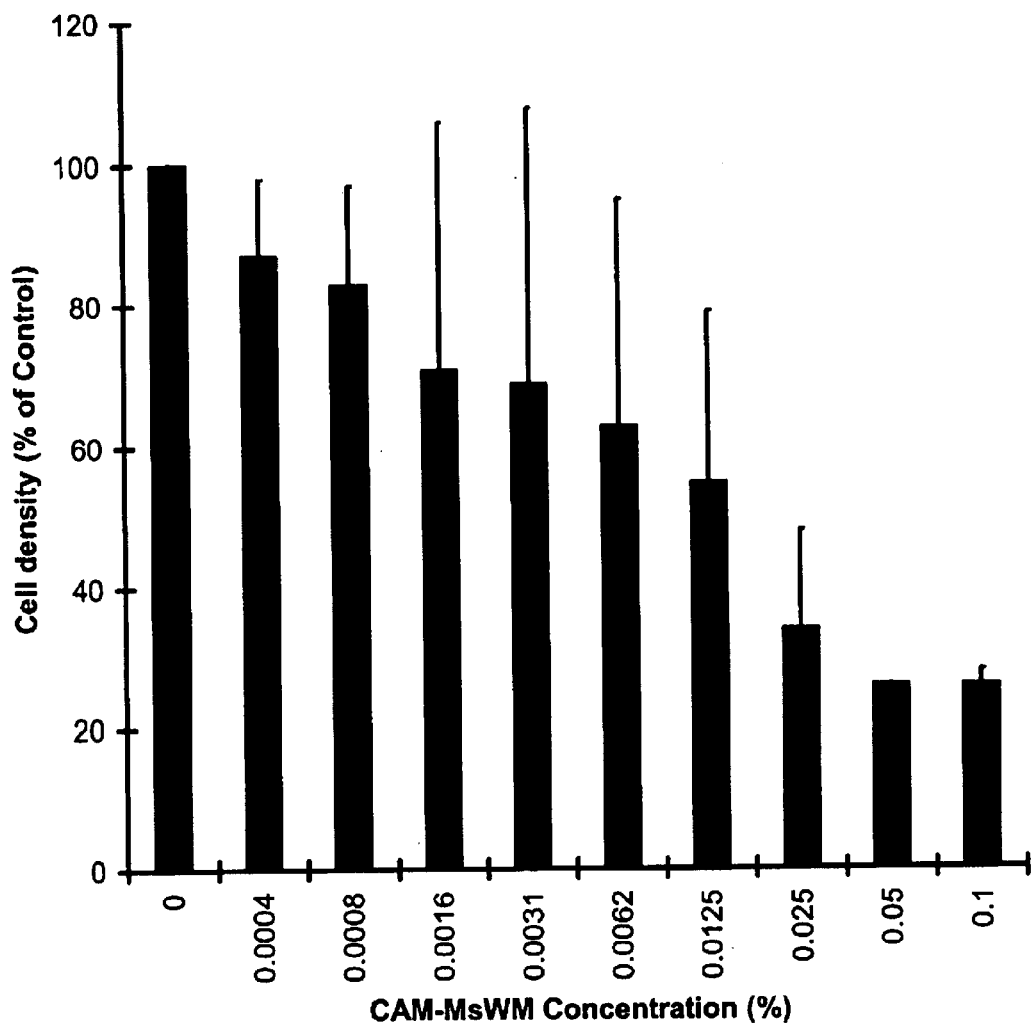
FIG. 2: represents a graph of the results obtained by treating MDA-435 cells with different concentrations of a cell medium extract of *Hagenia abyssinica* (CAM-MsWM).
Figure 3:
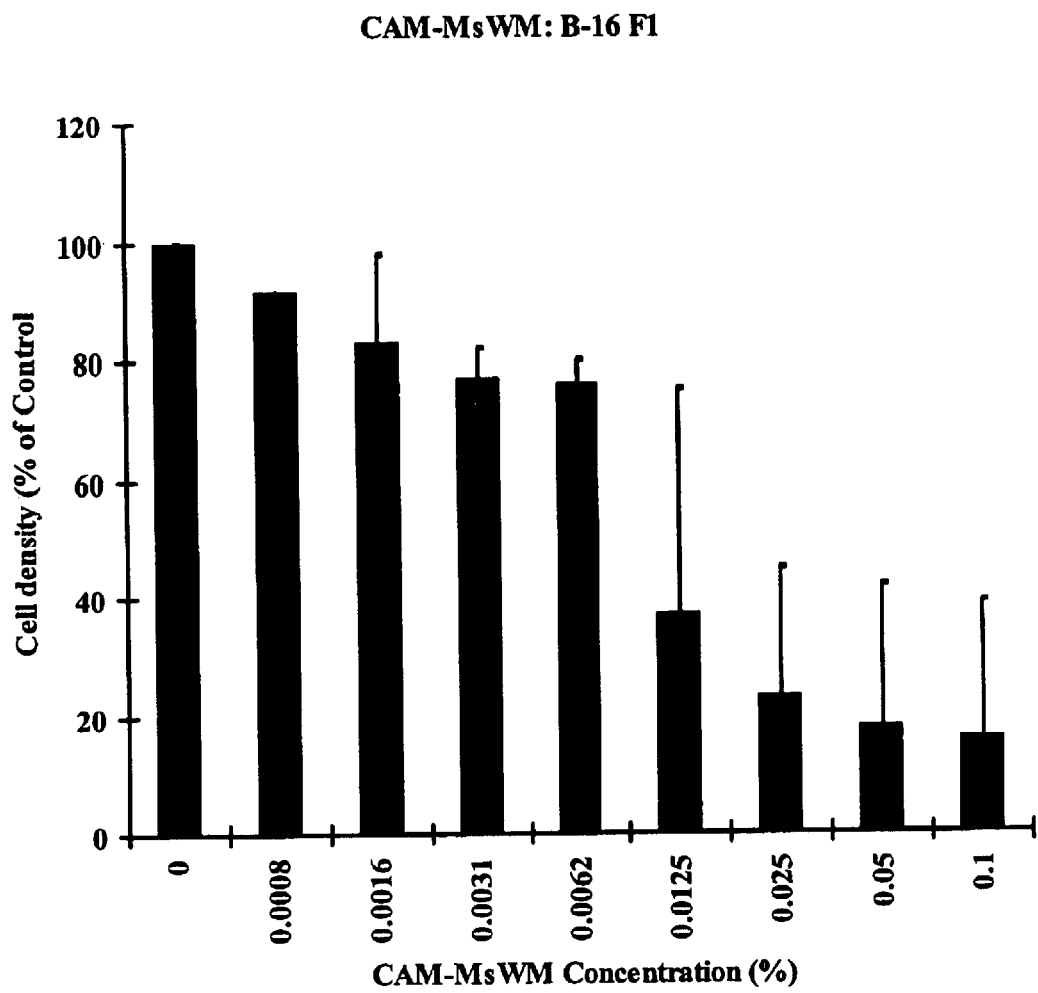
FIG. 3: represents a graph of the results obtained by treating B16-F1 cells with different concentrations of cell medium extract of *Hagenia abyssinica* (CAM-MsWM).
Figure 4:
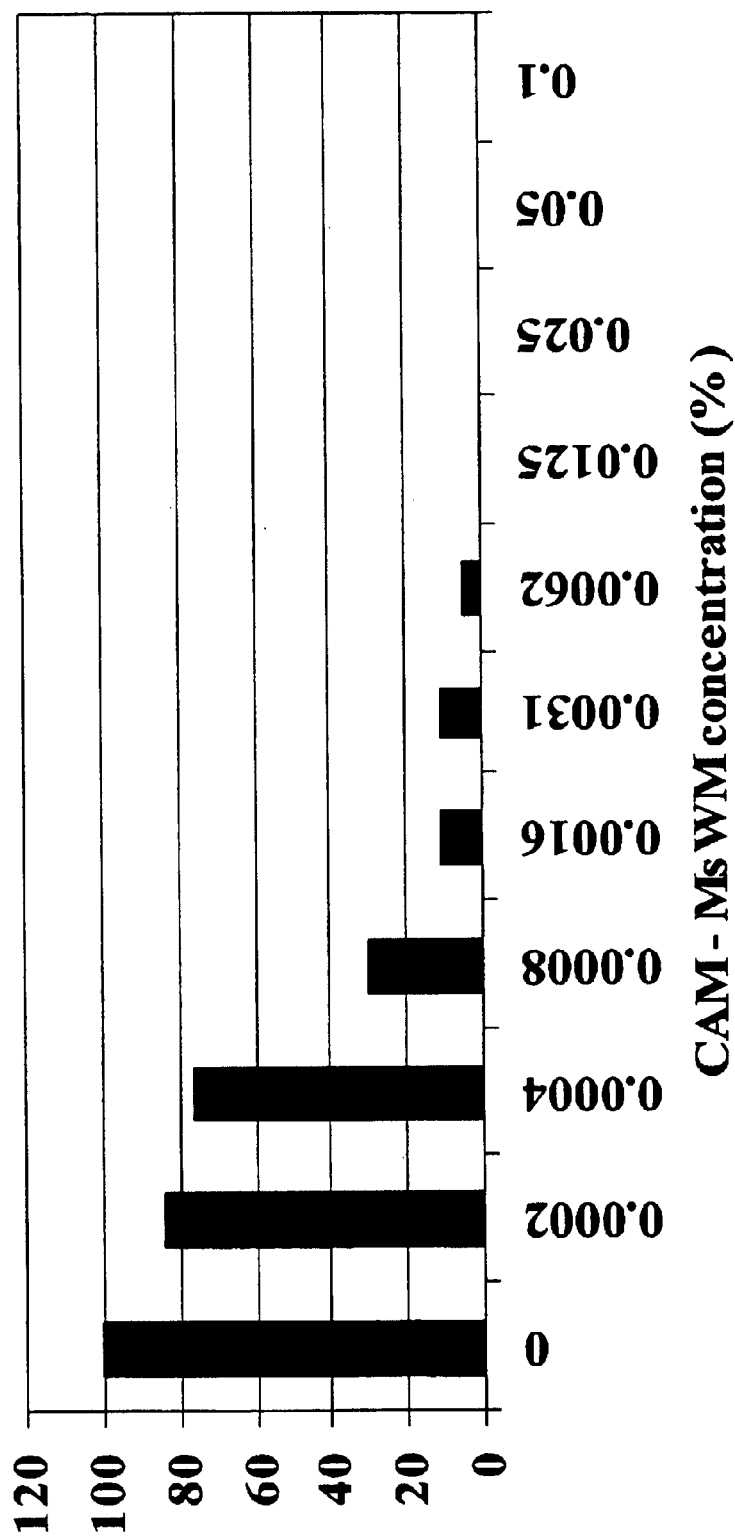
FIG. 4: represents a graph of the results obtained by treating MCF-7 cells with different concentrations of a cell medium extract of *Hagenia abyssinica* (CAM-MsWM).
Figure 5:
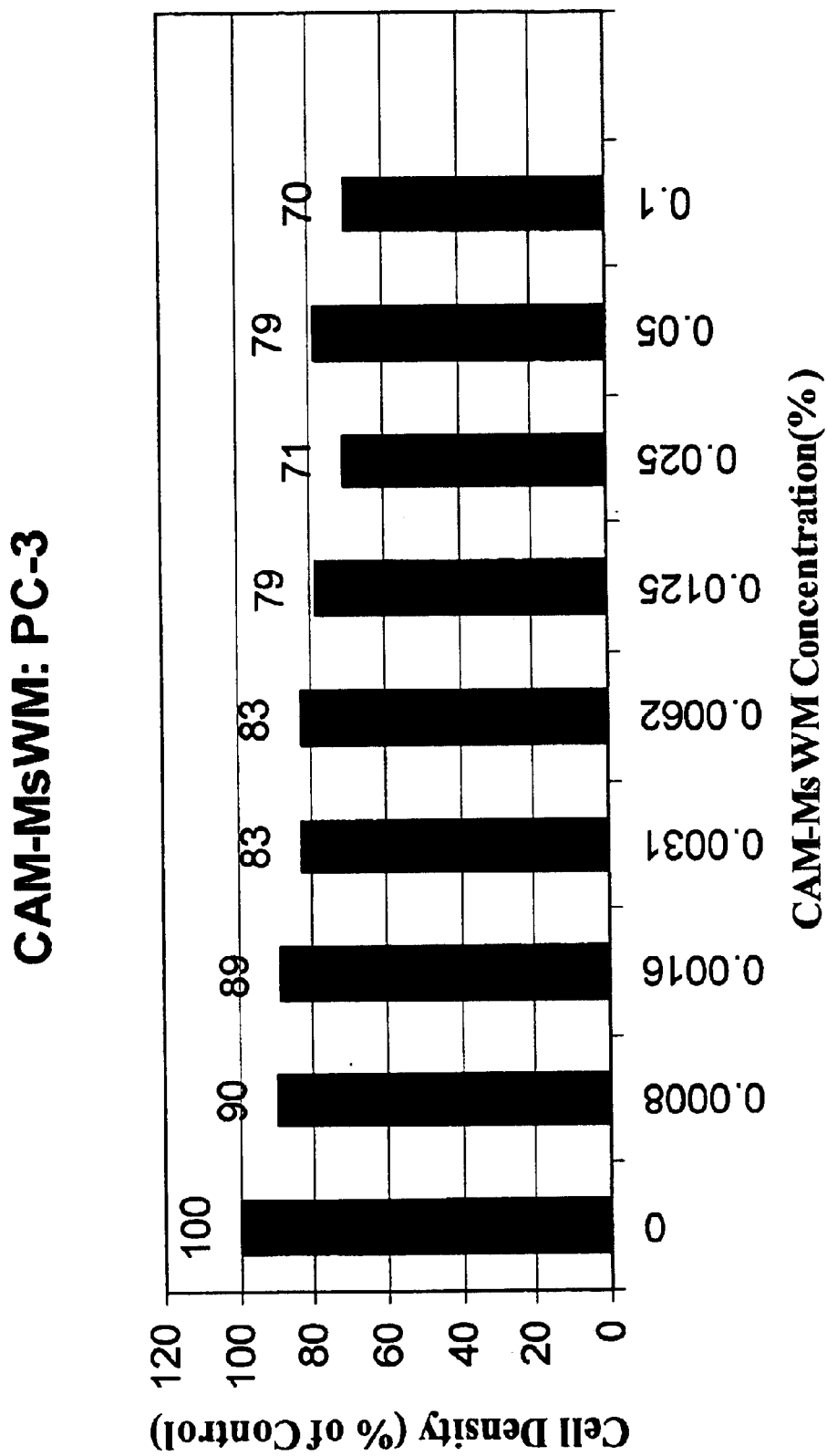
FIG. 5: represents a graph of the results obtained by treating PC-3 cells with differing concentrations of a cell medium extract of *Hagenia abyssinica* (CAM-MsWM).

Cytotoxity of the cell medium extracts of CAM-MsWM was also evaluated by DYNE MRX. To accomplish this, 20 μls of Almarblue was added to each well of the test plate, incubating at 37° C. for at least four hours, and reading the oxidation level by DYNE MRX. FIGS. 2 though 5 represent graphs of the relative inhibitory effect of the different concentrations of a non-serum DMEM extract of *Hagenia abysinnica* (CAM-MsWM) on the growth of cancer cells of various types, including MDA-435, B16F1, MCF-7, and PC3. FIG. 2 demonstrates that the toxicity of CAM-MsWM on the MDA435 cells appears to decrease with the concentration tested. FIG. 3 demonstrates that the CAM-MsWM was most effective on the B16F1 cell line at concentrations from 0.025 to 0.1%. While not particularly inhibitory at concentrations between 0.008 and 0.0062%, CAM-MsWM also displayed a reasonable level of activity at the mid-range concentration of 0.125%. FIG. 4 demonstrates the toxicity of a non-serum DMEM extract of CAM-MsWM on MCF-7 cells. FIG. 5 depicts the effect of a non-serum DMEM extract CAM-MsWM on PC-3 cells. While this compound does not appear to have a marked effect on these cells, some reduction of cancer cell growth was observed. The lowest cancer cell density was observed at the highest concentration of CAM-MsWM, thus, potentially higher concentrations of the extract may induce more dramatic cytotoxic effects.

EXAMPLE 5
Cytotoxicity of CAM-YING CAM-YING, the 0.1% plant extract prepared in Example 1, was serially diluted for testing on cancer cells at different concentrations. 300 μls of CAM-YING was diluted with 300 μls of 10% serum DMEM (1:1 extract to serum). The serial dilution was continued by sequential addition to test tubes containing 300 μls of 10% serum DMEM (with Media RPMI 1640 was substituted for the 10% serum DMEM in the experiments performed with the MCF-7 cancer cell line). In each well of the test plate 150 μls of extract dilution was mixed with 20 μls of diluted cancer cells and incubated at 37° C. for 3–4 days. Cancer cell lines treated with CAM-YING include MDA-435 (breast), B16F1 (myeloma), MCF-7 (breast) and PC3 (prostate).

Figure 9A:
FIG. 9: depicts photomicrographs of MDA-435 cells treated with an extract of *Millettia ferruginea* prepared using a cell medium extractant. 9A represents the control. 9B and 9C represent a higher concentration (0.1–0.0125%) of the *Millettia ferruginea* extract, while 9D represents a lower concentration (0.0008 to 0.0004%).
Figure 9B:
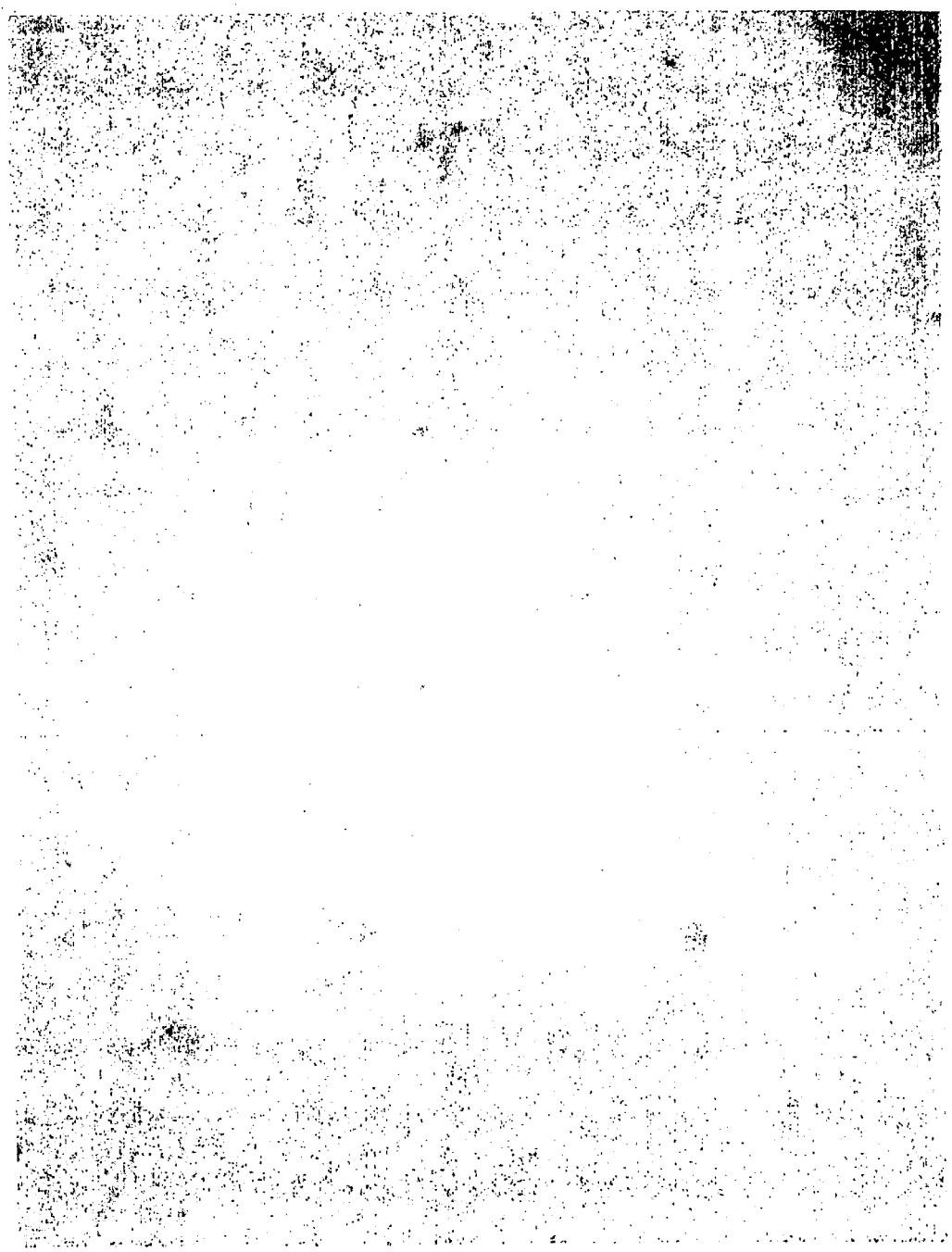
Figure 9C:
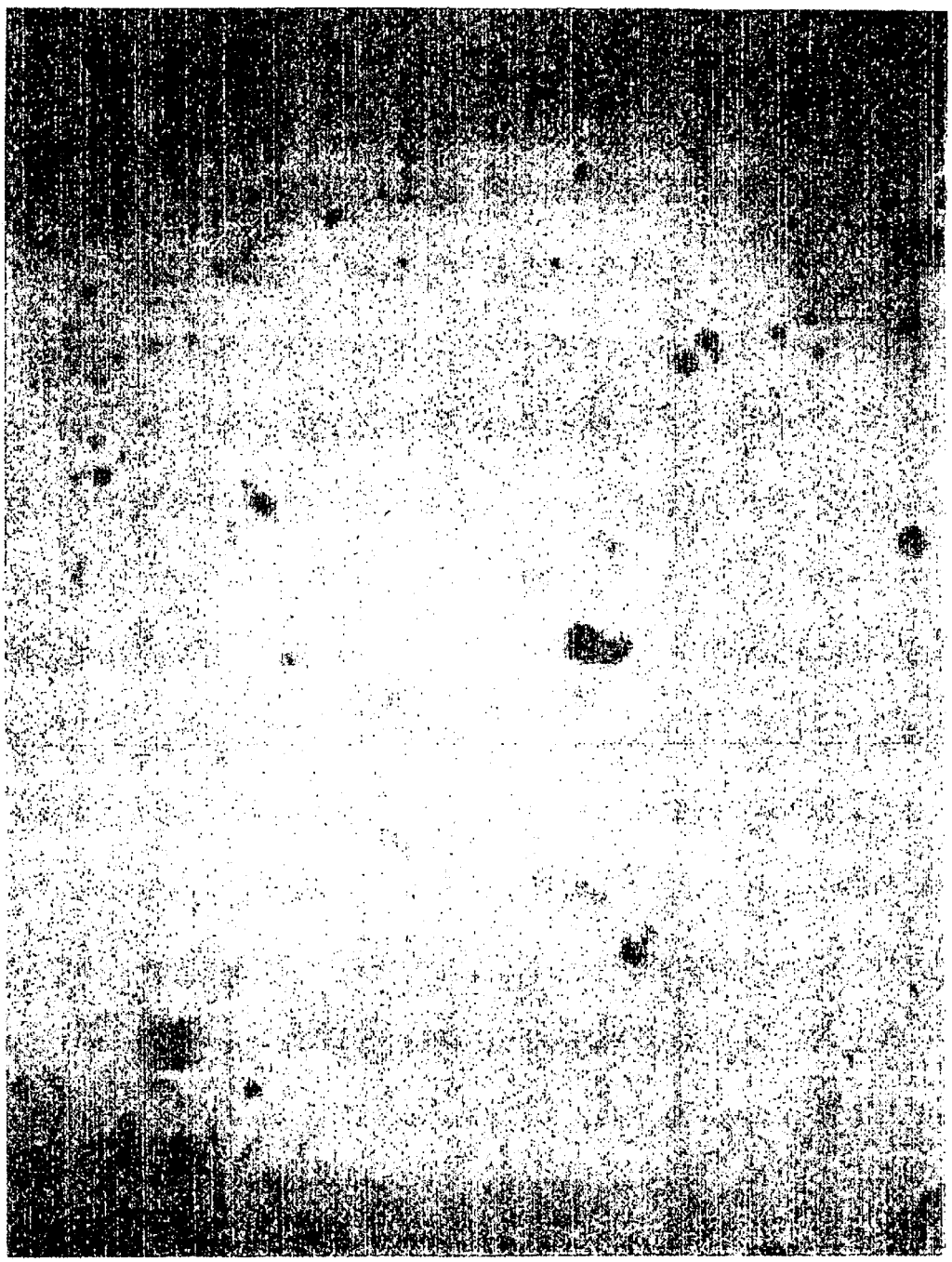
Figure 9D:
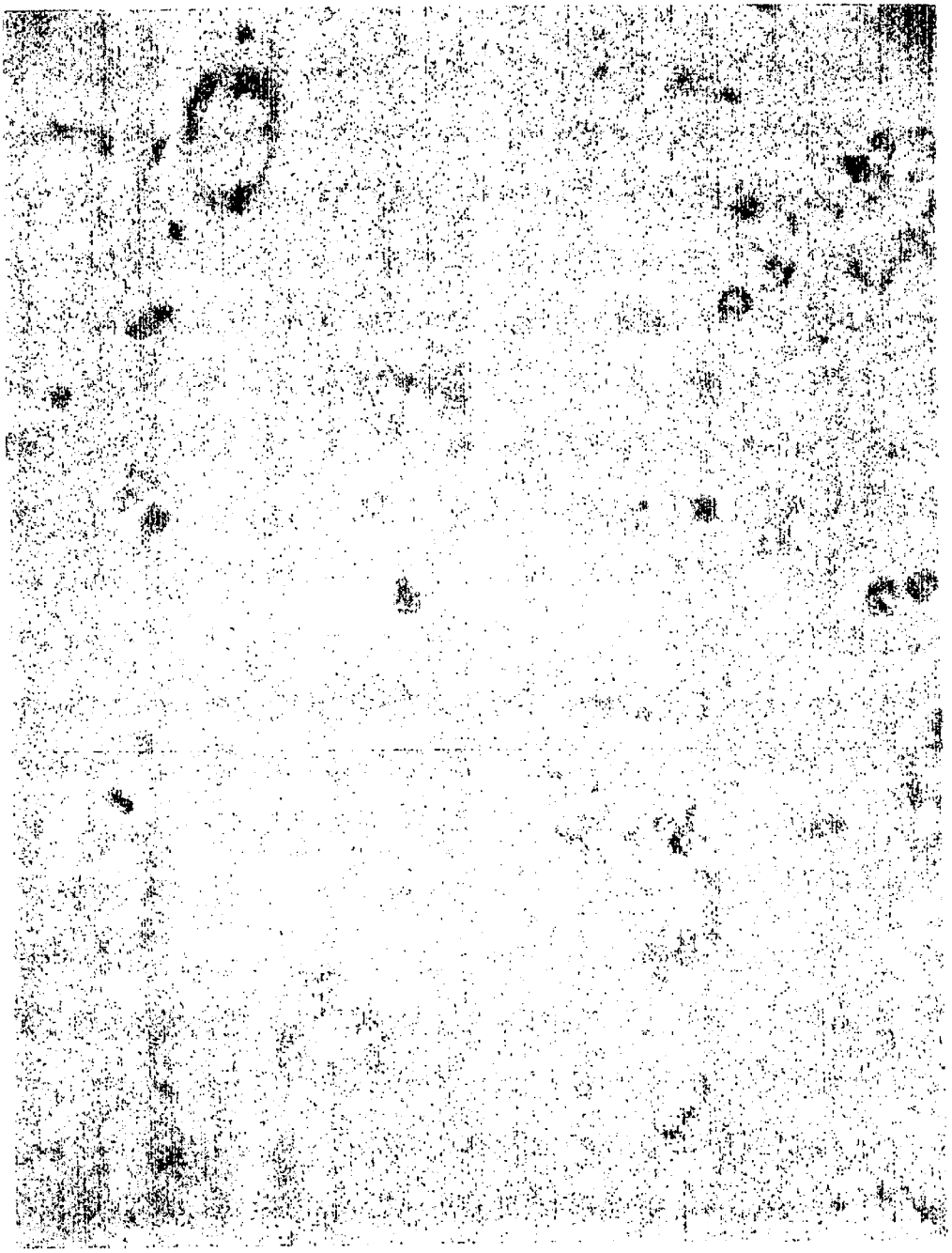

During this period, the cytotoxicity of the CAM-YING extract was observed by examination under the microscope. FIG. 9 represents photomicrographs of the effect of non-serum DMEM extract of Millettia ferruginea (CAM-YING) on MDA-435 cells. 9A represents the control, while FIGS. 9A though 9B depict the effects of various concentrations of CAM-YING on the MDA-435 cells. FIGS. 9B and 9C represent the effect of a higher concentration (0.1–0.0125%), while FIG. 9D depicts the effect of a lower concentration (0.0008–0.0004%). FIG. 9 demonstrates that cell density tends to decrease with higher concentrations of CAM-YING.

Figure 10:
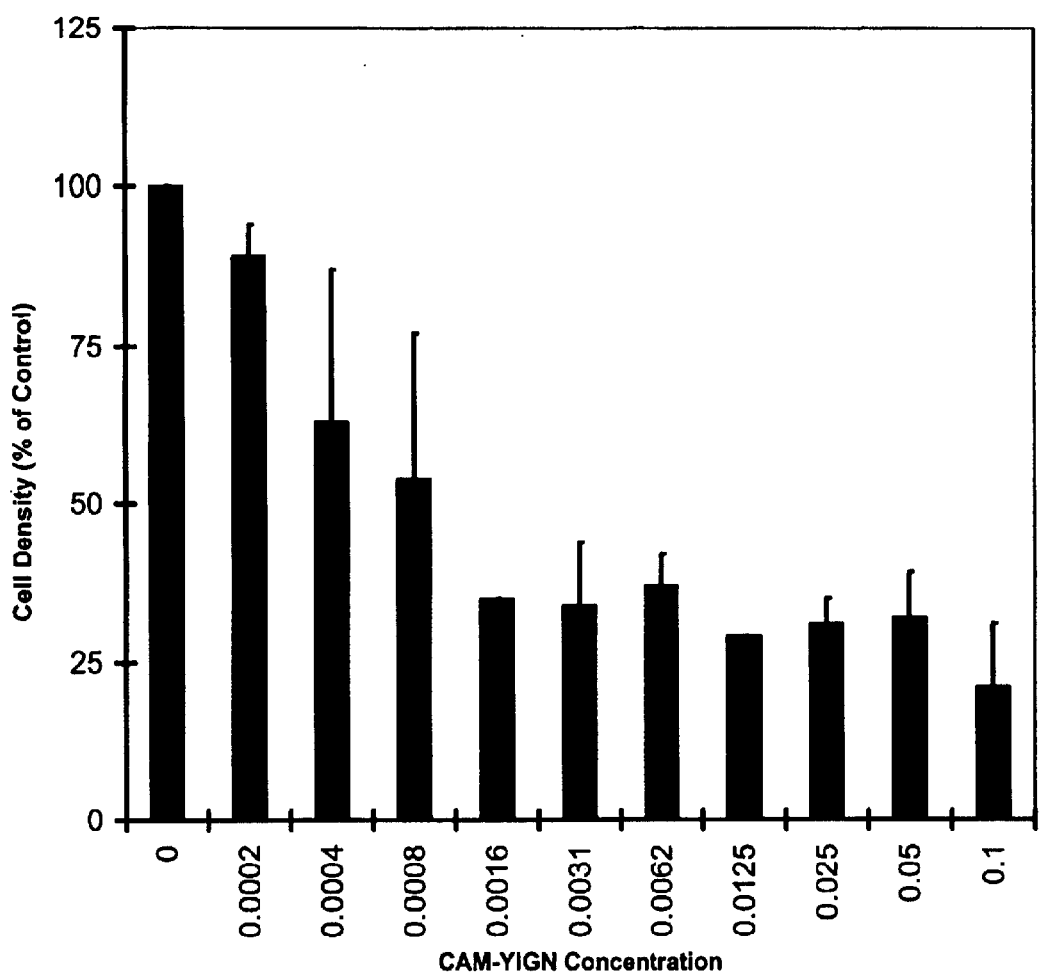
FIG. 10: represents a graph of the results of treating MDA-435 cells with differing concentrations of a cell medium *Millettia ferruginea* extract (CAM-YING).

Cytotoxity was also evaluated by DYNE MRX. To accomplish this, 20 μls of Almarblue to each well of the test plate, incubating at 37° C. for at least four hours, and reading the oxidation level by DYNE MRX. FIG. 10 represents a graph of the effect of increasing concentrations of the non-serum DMEM extract CAM-YING on the growth of MDA-435 cells. While the cytotoxic effect appears to increase sharply from 0.00020–0.0016%, it appears to level off somewhere between 0.0016% and 0.05%. CAM-YING displays the highest level of cytotoxicity at 0.1%, the highest concentration tested.

Figure 11:
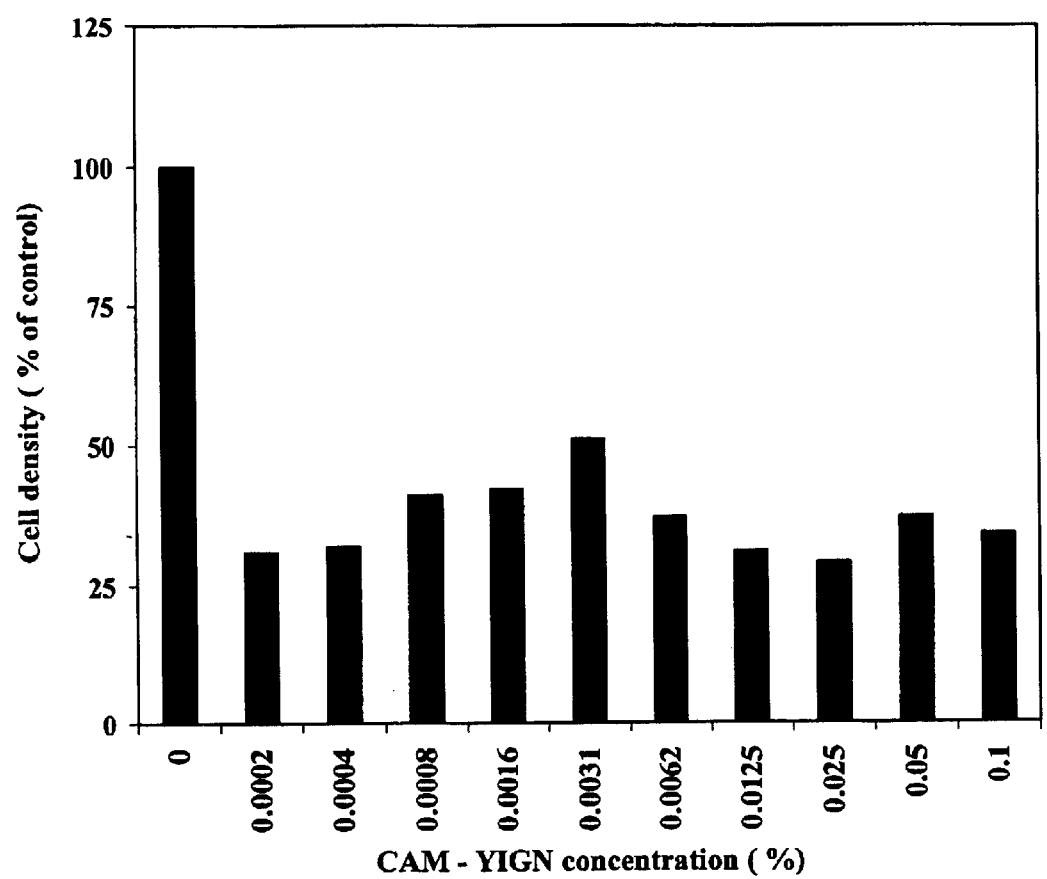
FIG. 11: represents a graph of the results of treating B16-F1 cells with differing concentrations of a cell medium *Millettia ferruginea* extract (CAM-YING).

CAM-YING exhibits a different pattern of activity against the B16F1 cell line, as shown in FIG. 11 demonstrating that CAM-YING displays the highest cytotoxic effect at the lower concentration of 0.0002–0.0003%, and at the higher concentrations of between 0.0125% and 0.1%. The least amount of activity was observed at the middle concentrations. Overall, however, CAM-YING exhibited a fairly strong toxic effect on B16FA, as compared to the control.

Figure 12:
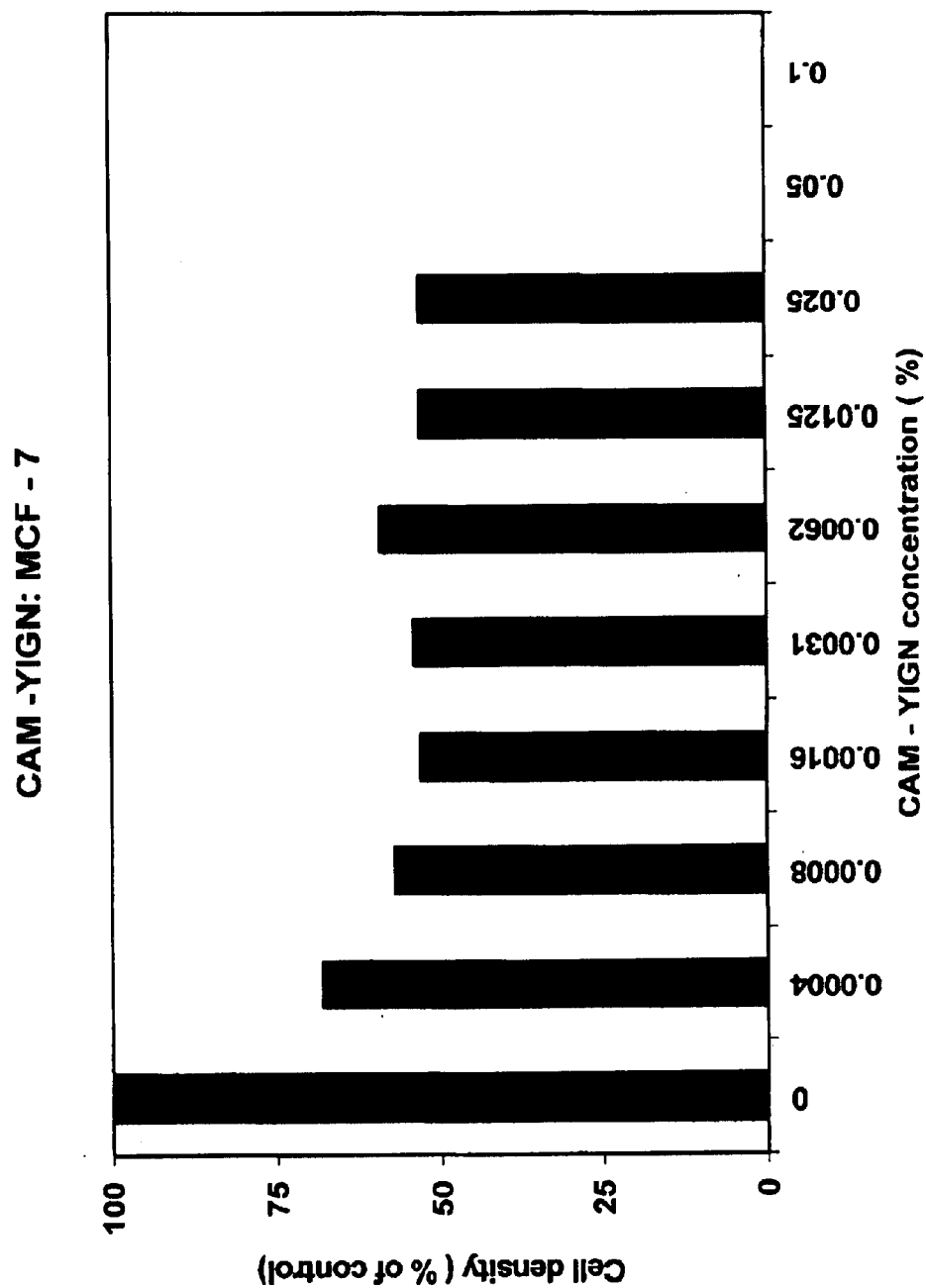
FIG. 12: represents a graph of the results of treating MCF-7 cells with differing concentrations of a cell medium *Millettia ferruginea* extract (CAM-YING).

The effects of CAM-YING on MCF-7 are shown in FIG. 12.

FIG. 13 illustrates the effects of CAM-YING on PC-3 cells. The results demonstrate that although the extract does appear to have a cytotoxic effect on the PC-3 cancer cells, the effect does not appear to vary tremendously with the concentration of the extract tested. However, the lowest cell density was observed with a CAM-YING concentration of 0.1%, the highest concentration tested.

EXAMPLE 6
Cytotoxicity of CAM-ANQZ

CAM-ANQZ, the 0.1% plant extract prepared in Examples 1 and 2, was serially diluted for testing on cancer cells at different concentrations. 300 μls of CAM-YING was diluted with 300 μls of 10% serum DMEM (1:1 extract to serum). The serial dilution was continued by sequential addition to test tubes containing 300 μls of 10% serum DMEM (with Media RPMI 1640 was substituted for the 10% serum DMEM in the experiments performed with the MCF-7 cancer cell line). In each well of the test plate 150 μls of extract dilution was mixed with 20 μls of diluted cancer cells and incubated at 37° C. for 3-4 days. Cancer cell lines treated with CAM-ANQZ include MDA-435 (breast), B16F1 (myeloma), MCF-7 (breast) and PC3 (prostate).

Figure 14:
FIG. 14: depicts photomicrographs of the effects of treating MDA-435 cells with an organic solvent extract of *Ruta chalepensis*. 14A depicts the dense cell mass of the control. 14B and 14C depict the effect of differing concentrations of *Ruta chalepensis* extract on the cells, with 14B representing a higher concentration (between about 0.1–0.0125%) of the extract, and 14C representing a middle concentration (between about 0.0062–0.0016%).
Figure 14:
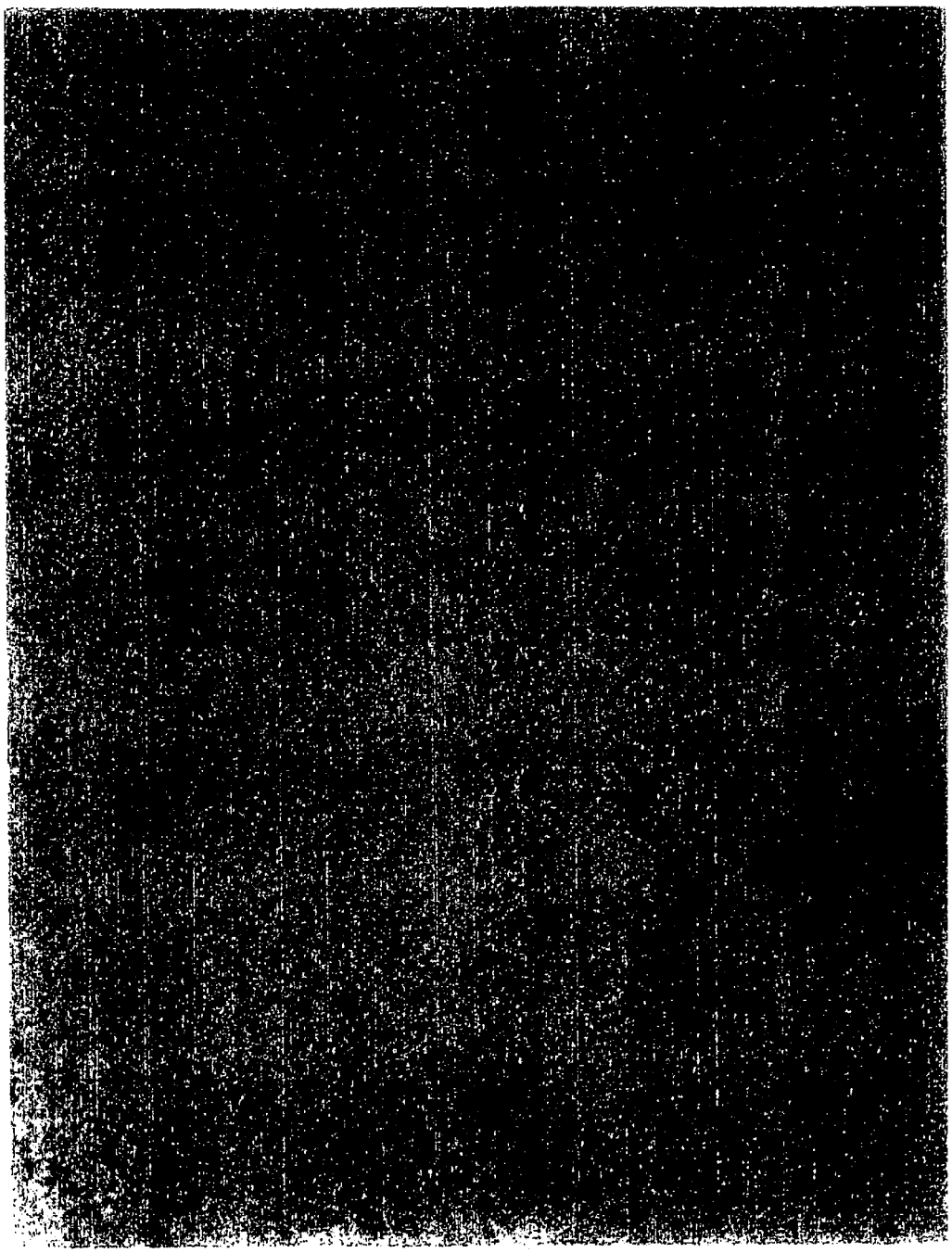
Figure 14:
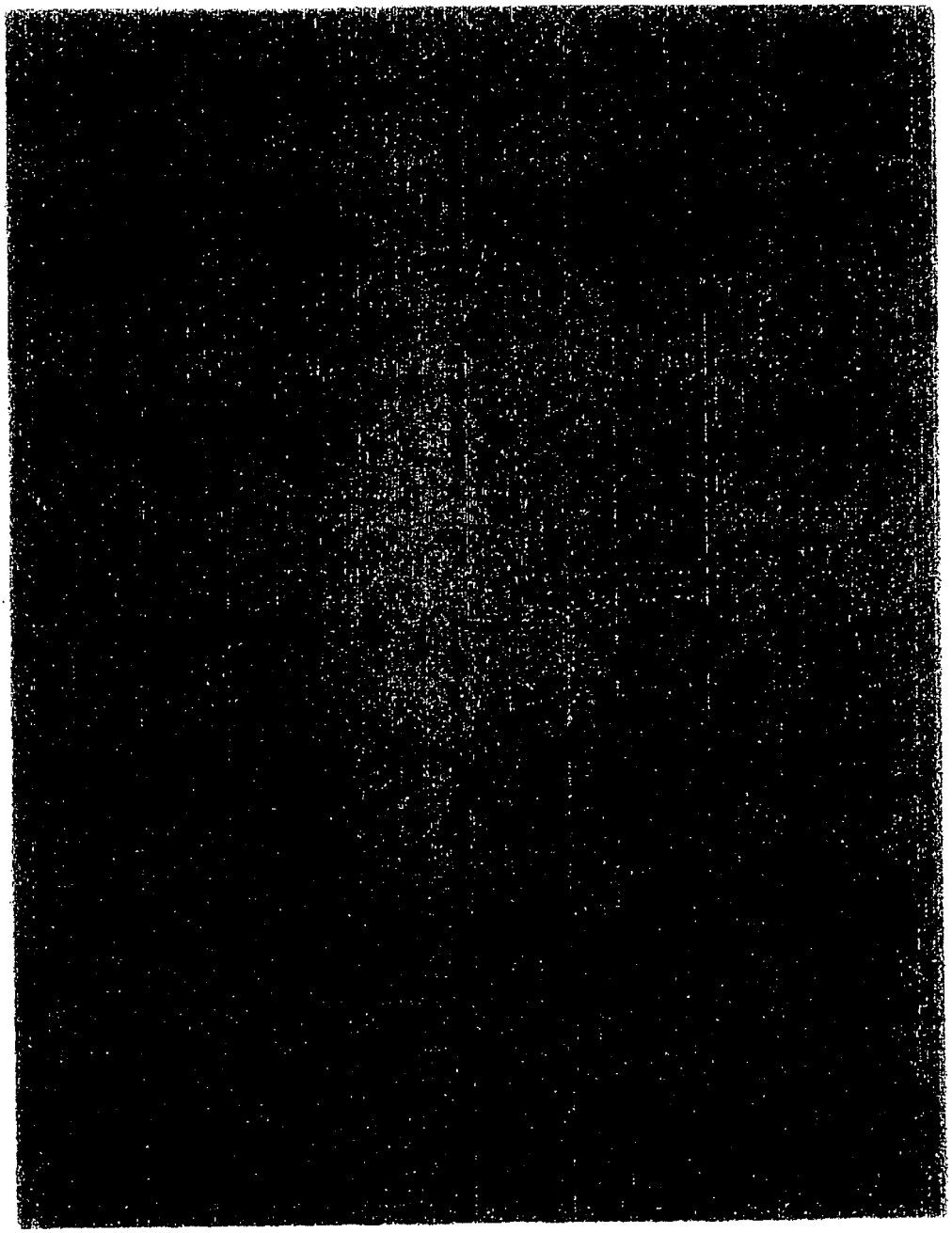

During this period, the cytotoxicity of the organic solvent CAM-ANQZ extract was observed by examination under the microscope. FIG. 14 depicts the effect of CAM-ANQZ on the MDA-425 cells. FIG. 14A shows the dense cell mass of the control. FIG. 14B represents the effect of a higher concentration (0.1-0.0125%) of CAM-ANQZ, while 14C depicts the effect of a middle concentration (0.0062-0.0016%) of CAM-ANQZ. There appears to be a greater cytotoxic effect with higher concentrations of CAM-ANQZ.

Figure 6:
FIG. 6: represents a graph of the results obtained by treating MDA-435 cells with differing concentrations of an acetone extract of *Ruta chalepensis* (CAM-ANQZ).
Figure 7:
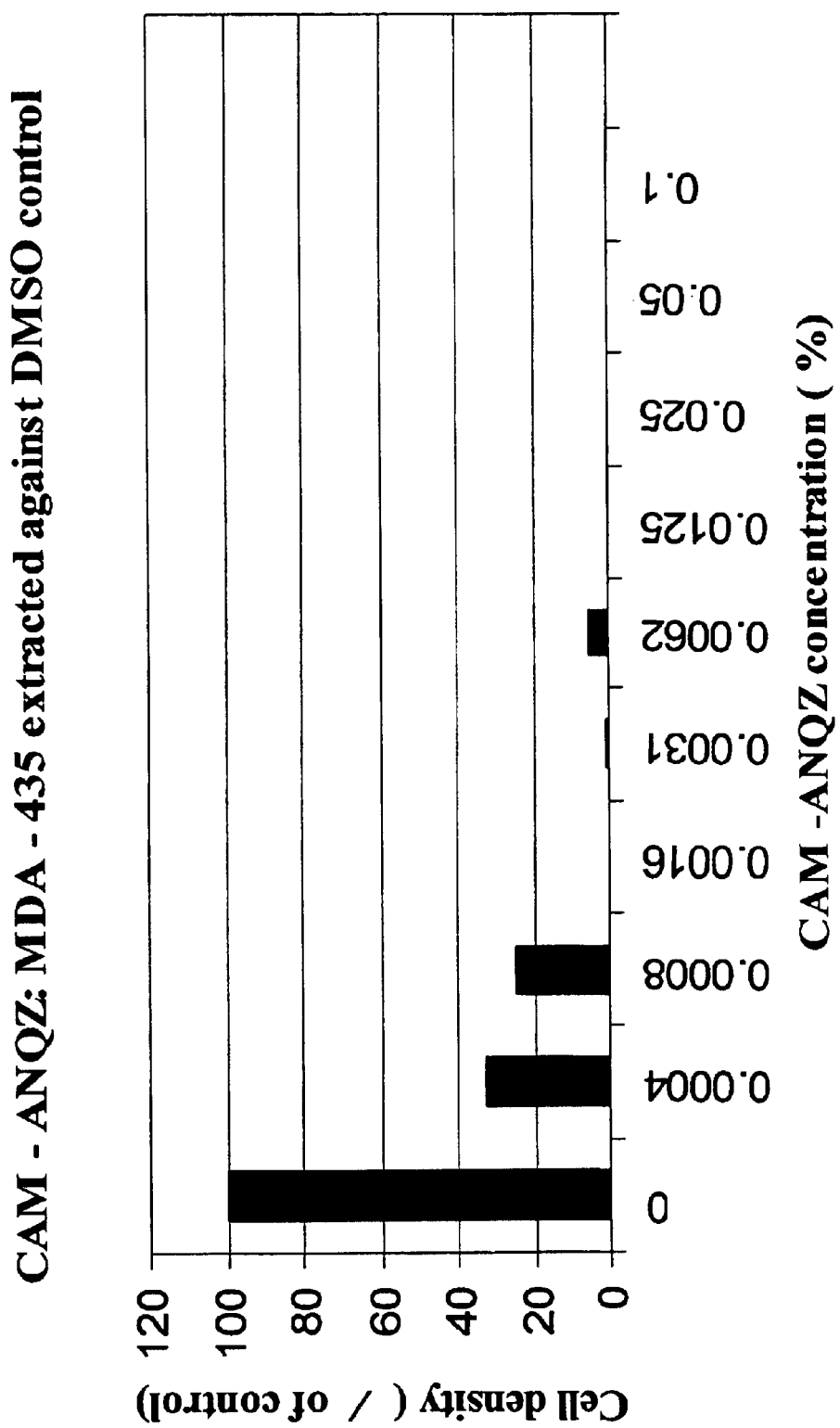
FIG. 7: represents a graph of the results obtained by treating MDA-435 cells with differing concentrations of a methanol extract of *Ruta chalepensis* (CAM-ANQZ).

Cytotoxicity was also evaluated by DYNE MRX. To accomplish this, 20 μls of Almarblue to each well of the test plate, incubating at 37° C. for at least four hours, and reading the oxidation level by DYNE MRX. FIGS. 6 and 7 represent the effects of an acetone extract of *Ruta chalepensis*, indicating a higher level of activity against cancer cells at higher concentrations (above 0.0016%). FIG. 7 represents the effects of a methanol extract of *Ruta chalepensis*, indicating a higher level of activity at higher concentrations (above 0.004%).

Figure 15:
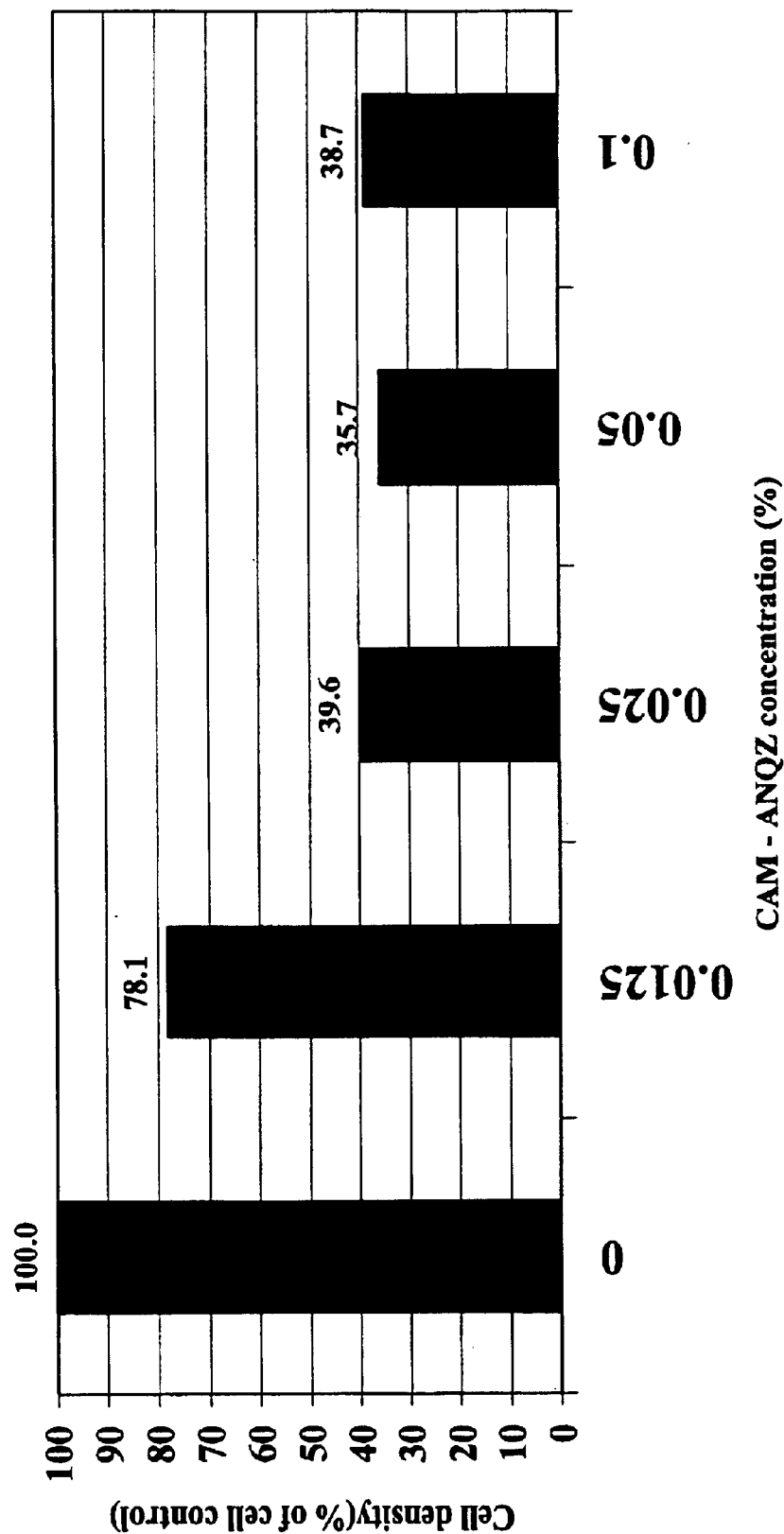
FIG. 15: represents a graph of the results of treating MDA-435 cells with differing concentrations of a cell medium *Ruta chalepensis* extract (CAM-ANQZ).
Figure 16:
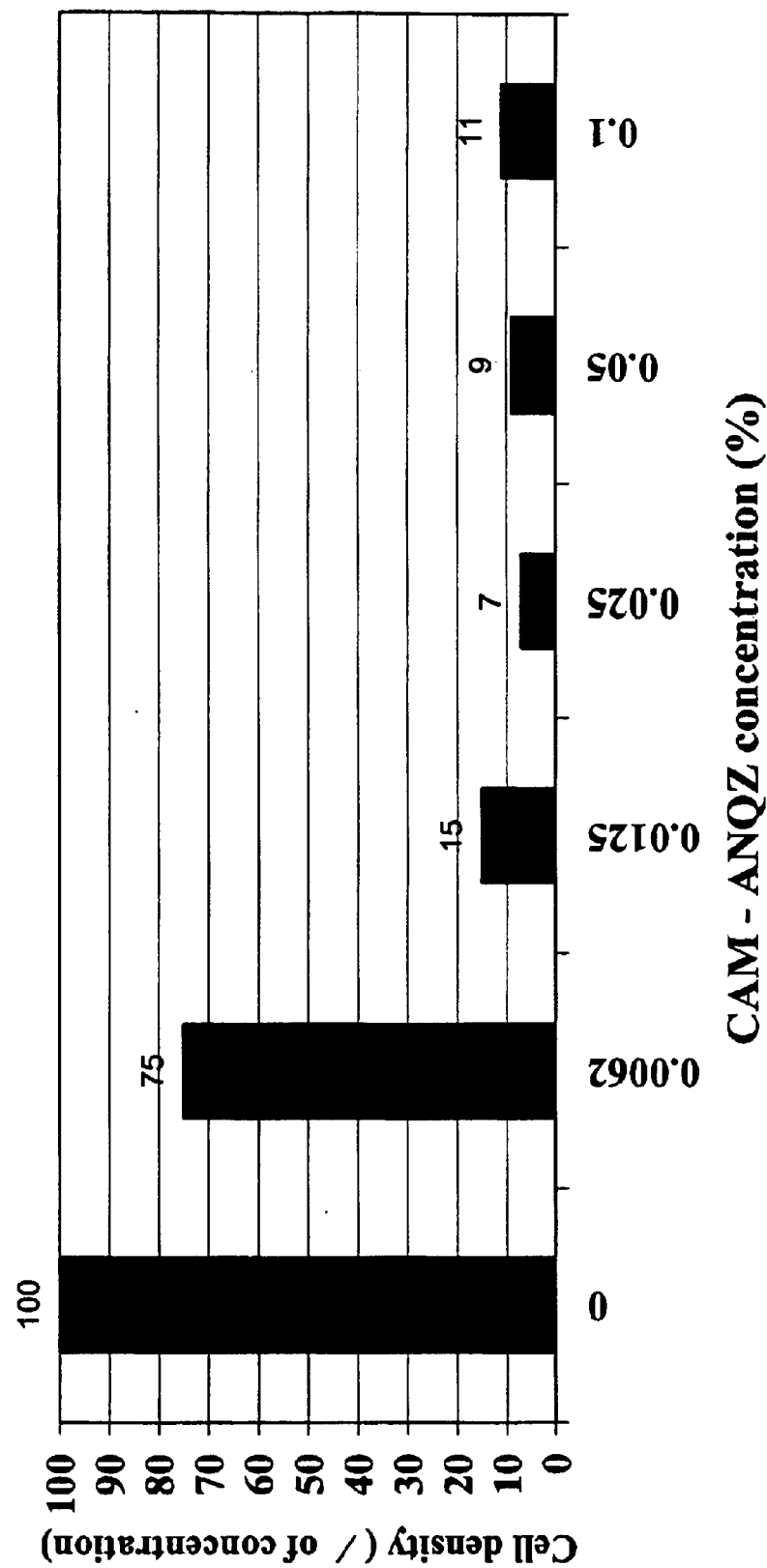
FIG. 16: represents a graph of the results of treating B16-F1 cells with differing concentrations of a cell medium *Ruta chalepensis* extract (CAM-ANQZ).
Figure 17A:
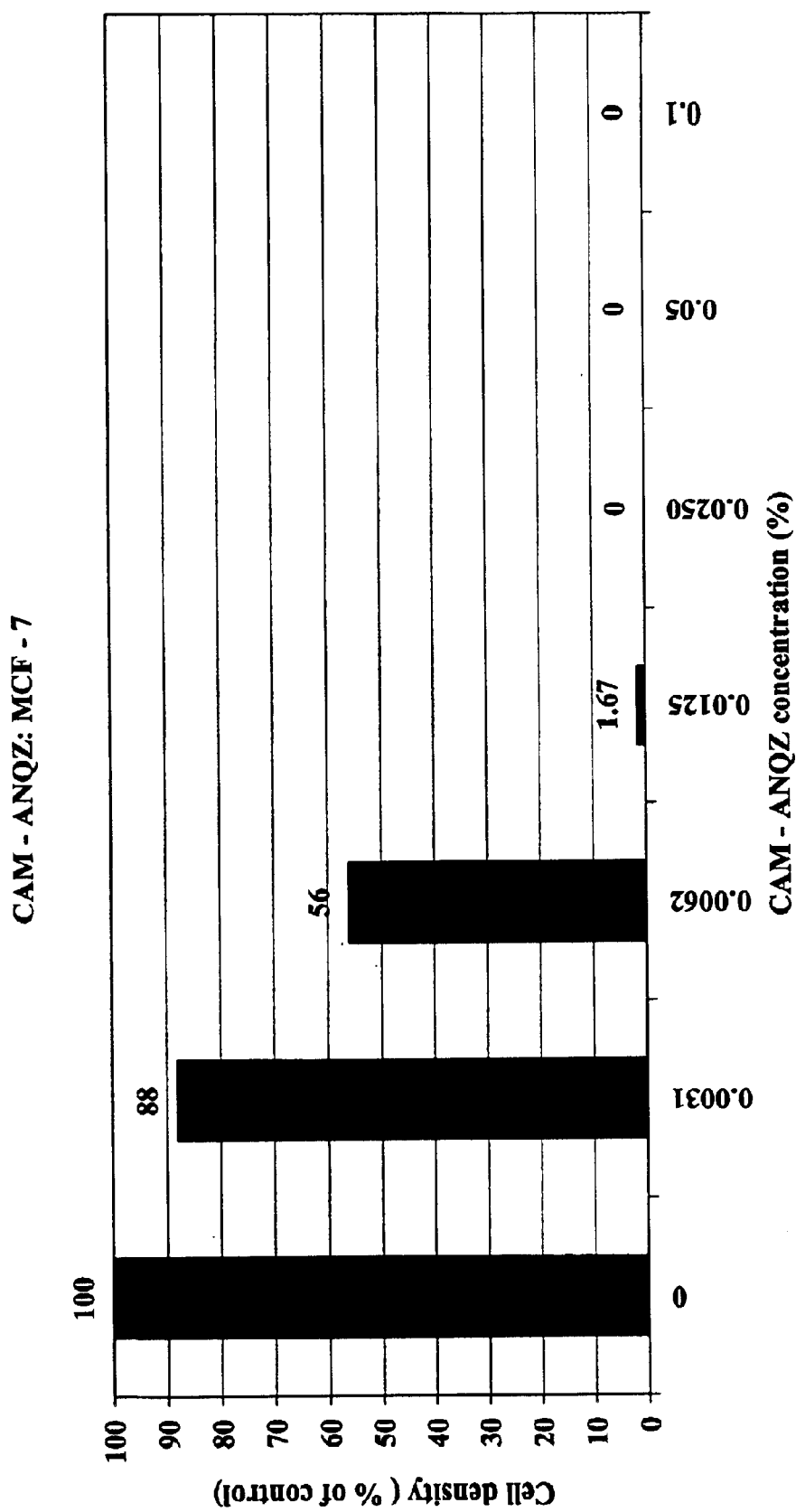
FIGS. 17A and 17B: represent graphs of the results of treating MCF-7 cells with differing concentrations of a cell medium *Ruta chalepensis* extract (CAM-ANQZ).
Figure 17B:
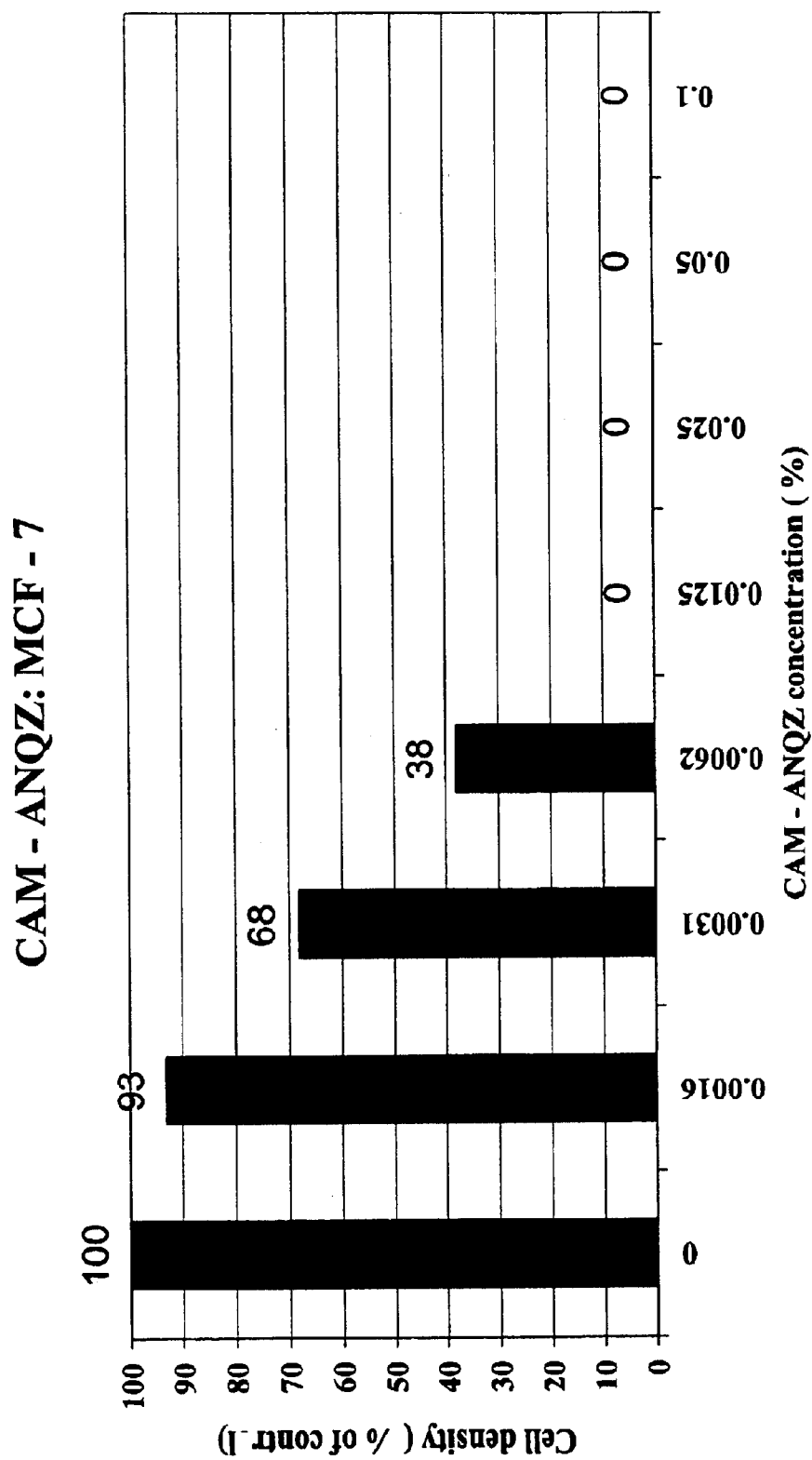

Cytotoxicity of the cell medium extracts was also evaluated by DYNE MRX. To accomplish this, 20 μls of Almarblue to each well of the test plate, incubating at 37° C. for at least four hours, and reading the oxidation level by DYNE MRX. FIG. 15 shows that the non-serum DMEM CAM-ANQZ appears to exhibit the highest cytotoxic activity against the MDA-435 cells at a concentration of from about 0.025 to 0.1%, with less anti-cancer activity at lower concentrations. FIG. 16 demonstrates the effects of non-serum DMEM CAM-ANQZ on the B16F1 cell line. CAM-ANQZ is shown to be most cytotoxic to cancer cells at concentrations in the range of 0.0125 to 0.1%. FIG. 17 demonstrates the effect of non-serum DMEM CAM-ANQZ on the MCF-7 cell line. This figure depicts that CAM-ANQZ displays a higher level of activity against the cancer cells at concentrations above 0.0062% percent.

Figure 18:
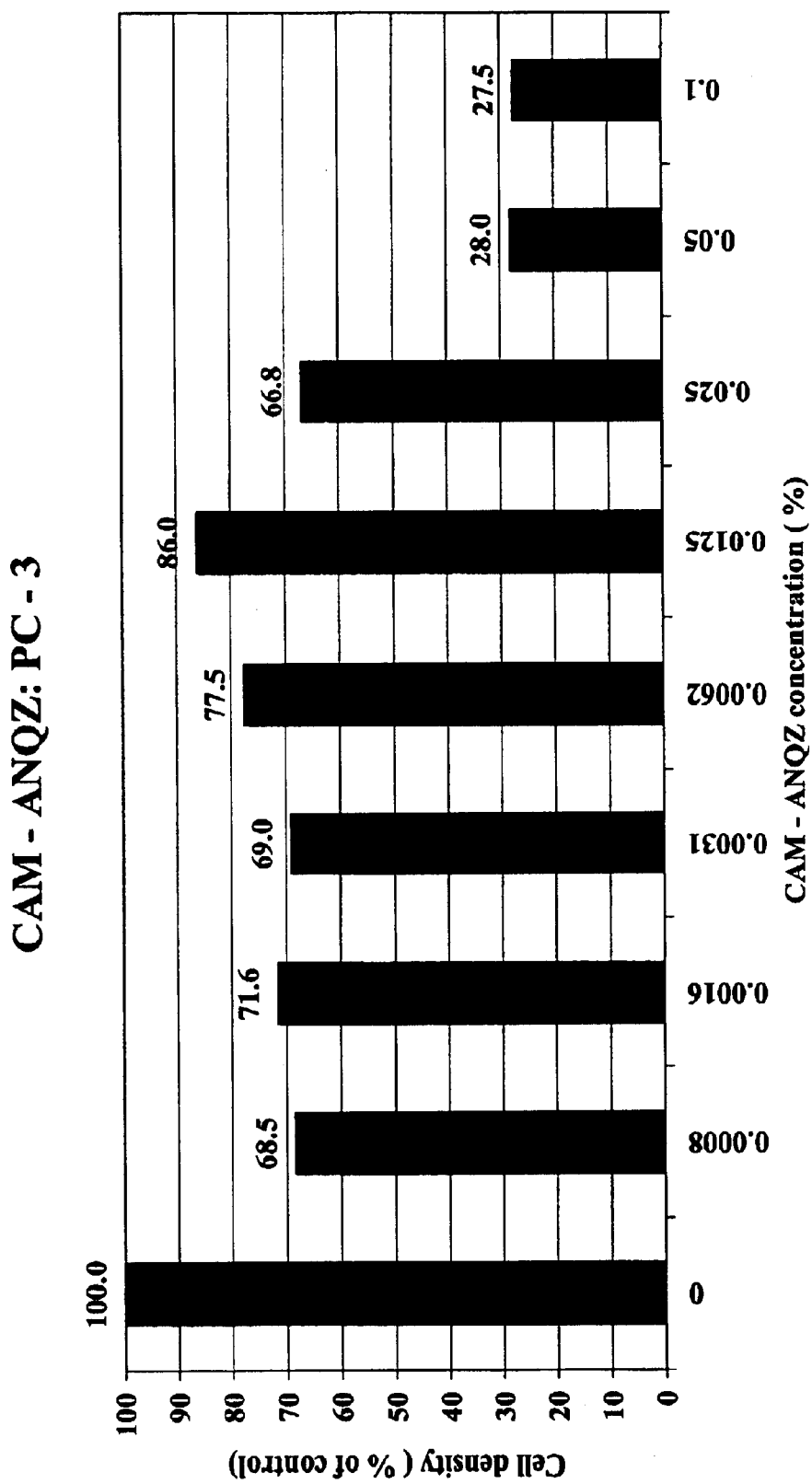
FIG. 18: represents a graph of the results of treating PC-3 cells with differing concentrations of a cell medium *Ruta chalepensis* extract (CAM-ANQZ).

FIG. 18 depicts the results of treating the PC3 cells with non-serum DMEM CAM-ANQZ. Various levels of anti-cancer activity are shown at various concentrations of CAM-ANQZ. The highest concentration tested obtained the best results, with the lowest cell density of cancer cells at concentrations of 0.5 to 0.1%.

EXAMPLE 7

A MsWM-CAMY3T 0.1% extract prepared in Example 1 was serially diluted for testing on MDA-435 breast cancer cells at different concentrations. 300 μls of MsWM-CAMY3T was diluted with 300 μls of 10% serum DMEM (1:1 extract to serum). The serial dilution was continued by sequential addition to test tubes containing 300 μls of 10% serum DMEM. In each well of the test plate 150 μls of extract dilution was mixed with 20 μls of diluted MDA-435 cancer cells and incubated at 37° C. for 3-4 days.

Figure 19:
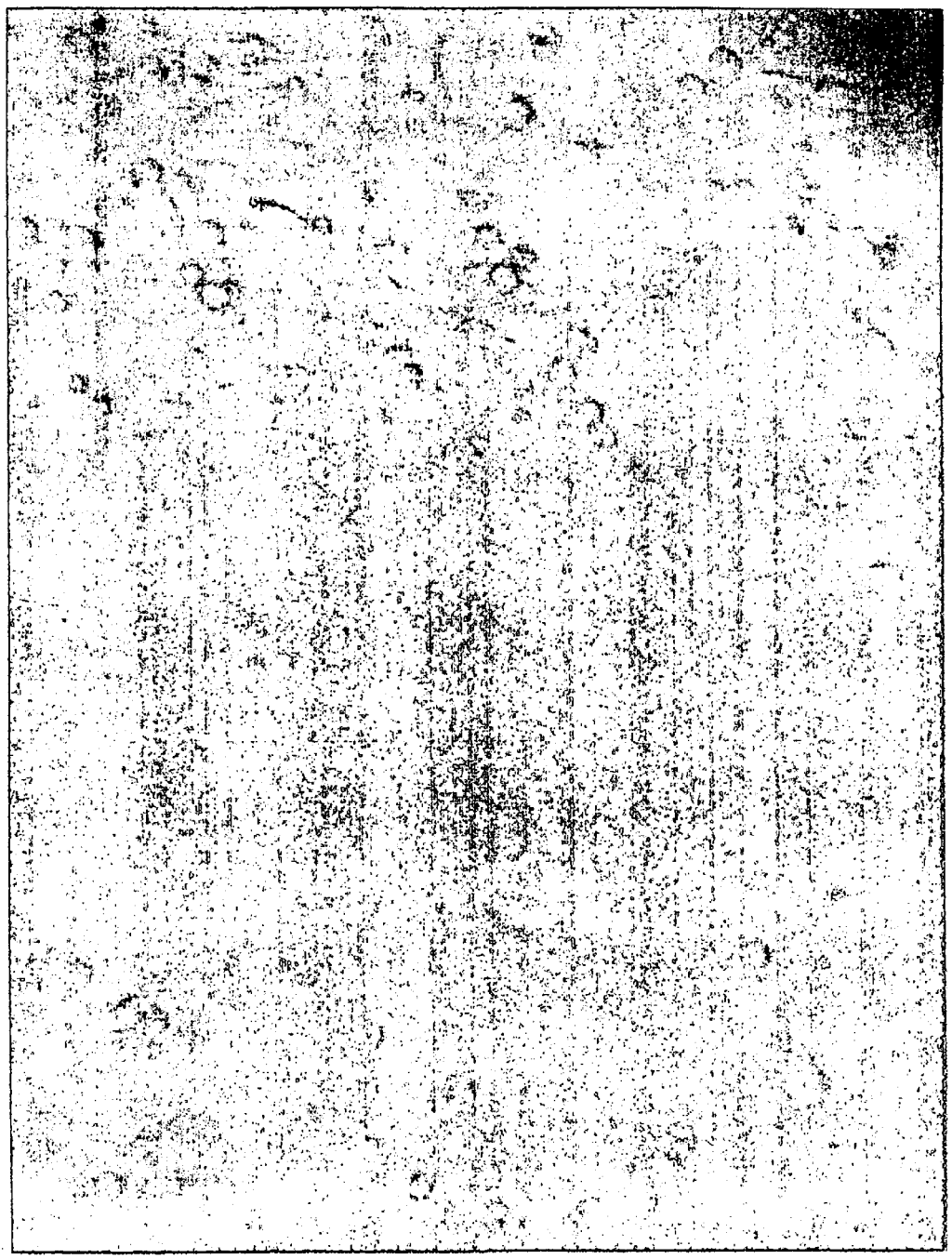
FIG. 19: depicts photomicrographs of the effects of treating MDA-435 cells with a cell medium extract of Glinus lotoides. 19A depicts the control. 19B-D depicts the effect of varying concentrations of *Glinus lotoides* extract on cancer cell growth. 19B and 19C represent the effect of higher concentrations (0.1–0.0125%) of the *Glinus lotoides* extract. 19D represents the effect of a lower concentration (0.0008 to about 0.0004%) of the *Glinus lotoides* extract.
Figure 19:
Figure 19:
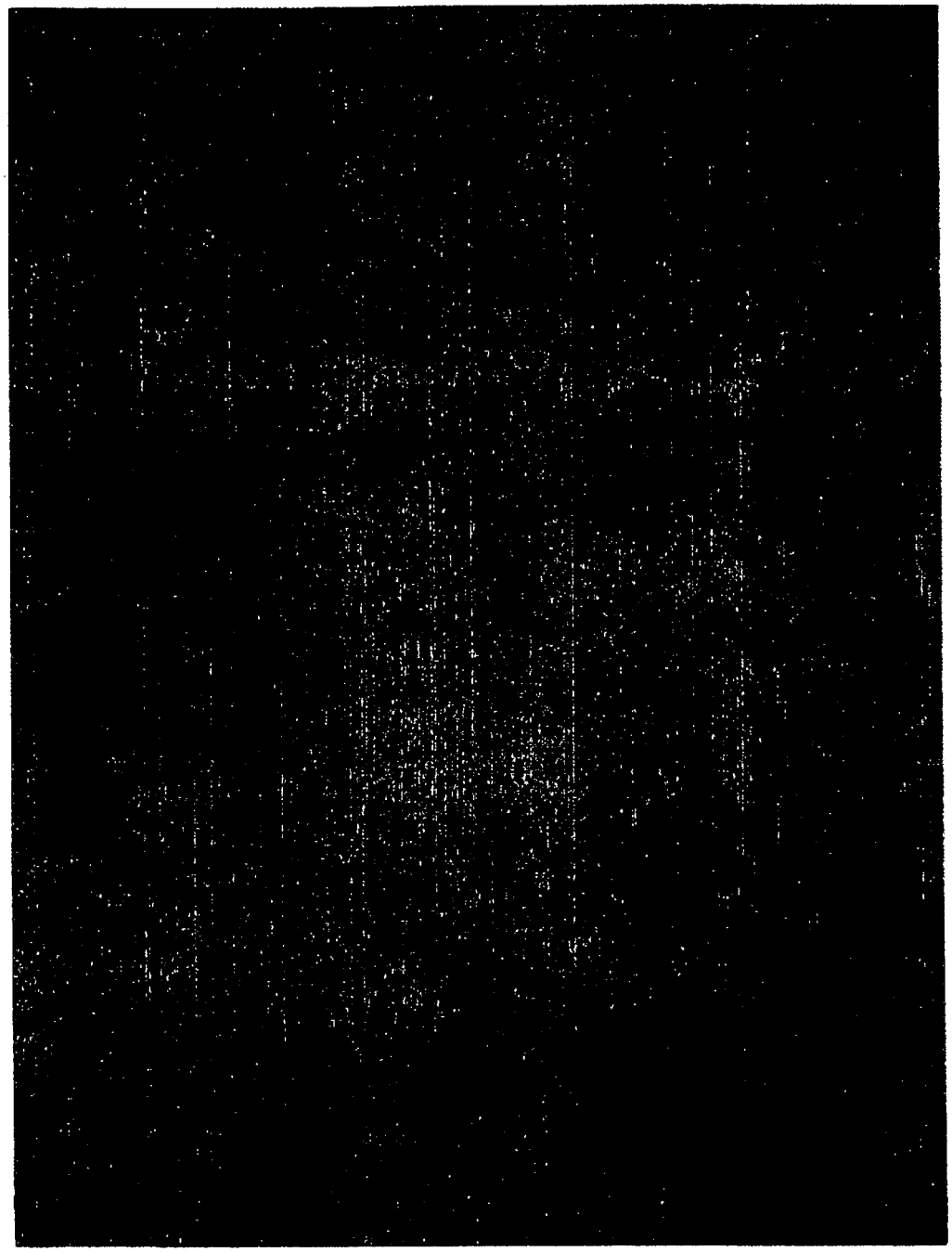
Figure 19:
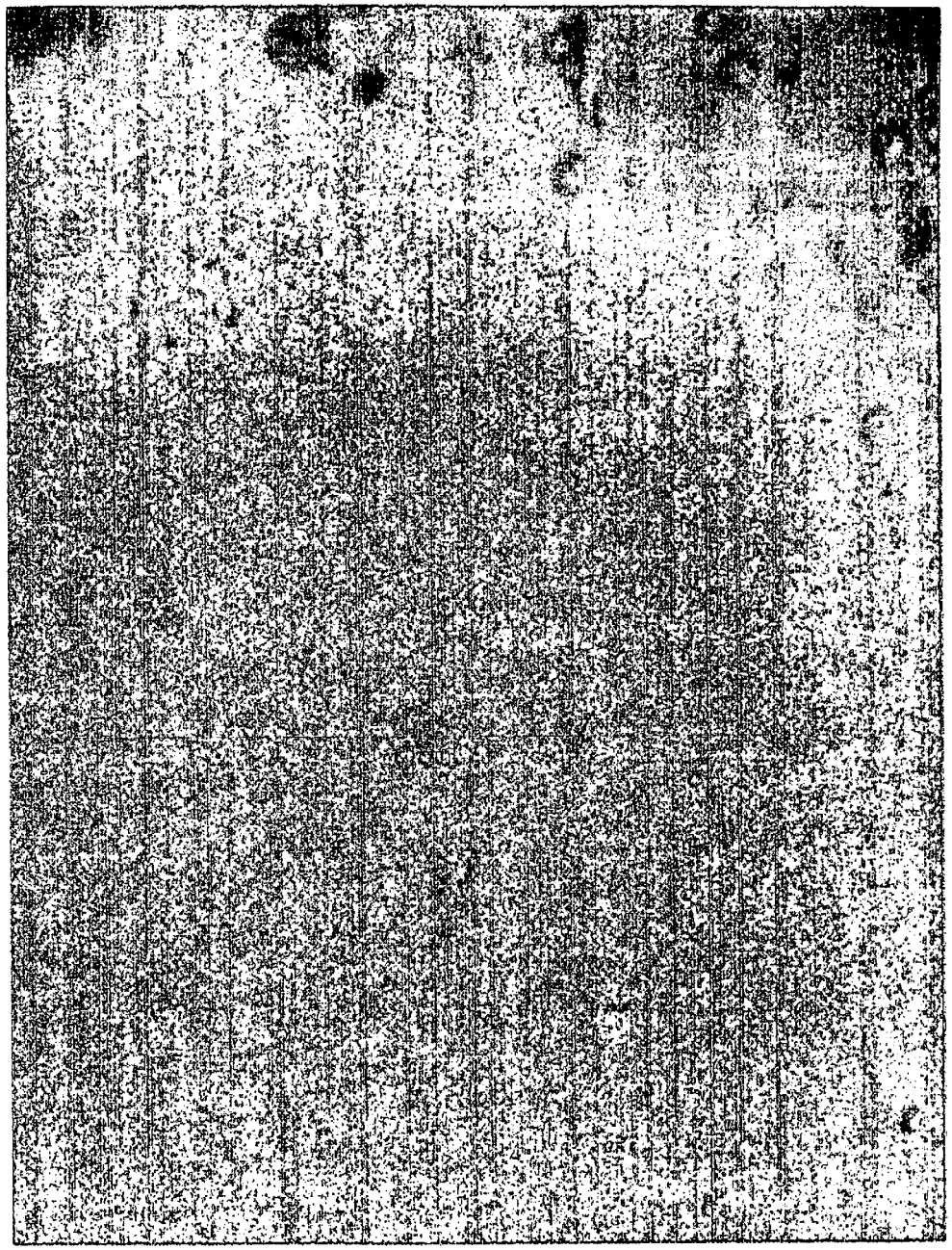

During this period, the cytotoxicity of the non-serum DMEM extract MsWM was observed by examination under the microscope. FIG. 19 depicts the results. FIG. 19A depicts the control for this experiment. FIGS. 19B-D represent the effects of varying concentrations of MsWM-CAMY3T on the cancer cell growth. More particularly, FIGS. 19B and C represent the effect of higher concentrations (0.1-0.0125%) of the MsWM-CAMY3T extract, while FIG. 19D represents the effect of a lower concentration (0.00080-0.0004%). Treatment with this compound appears to inhibit the proliferation of cancer cells.

Figure 20:
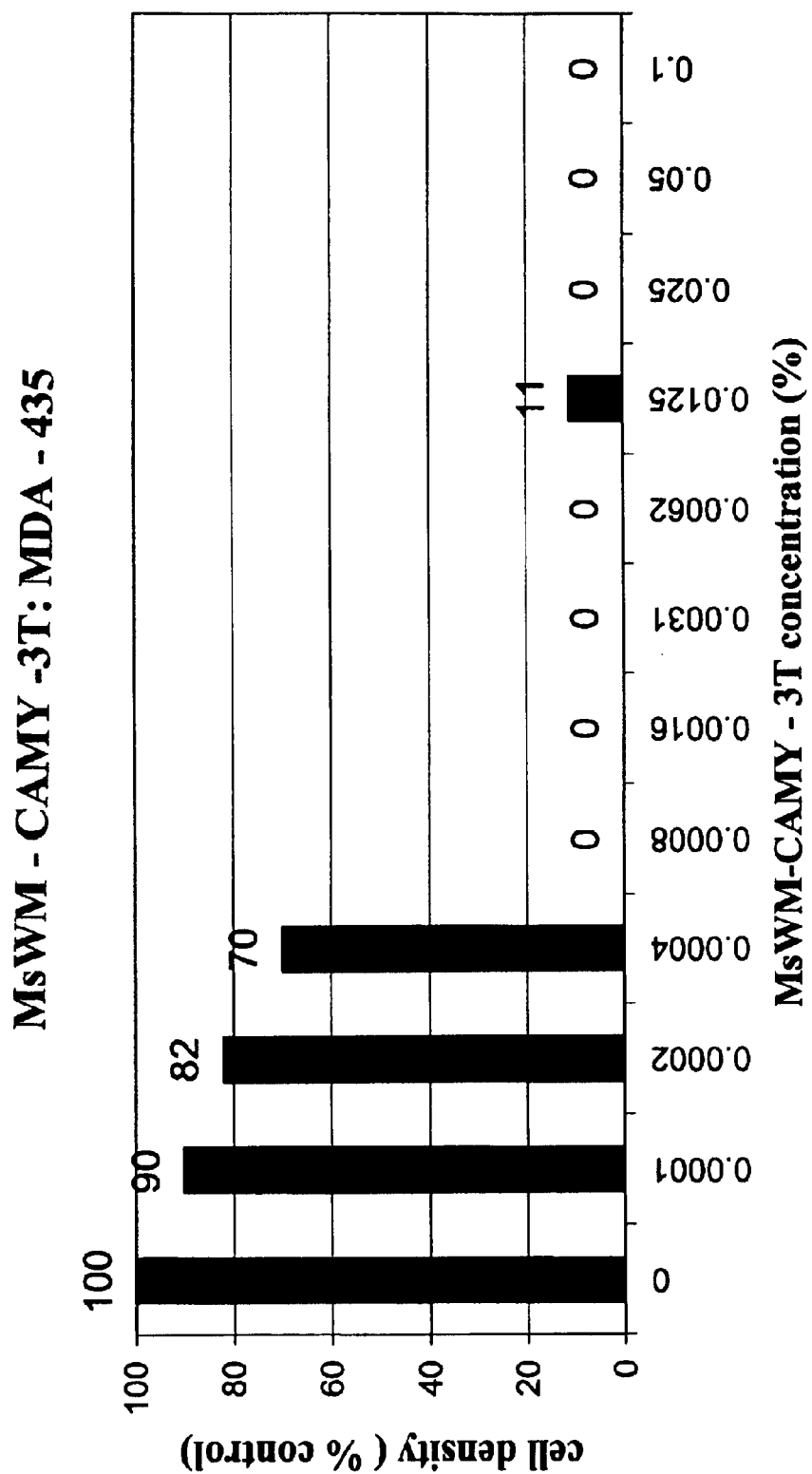
FIG. 20: represents a graph of the results obtained with treating MDA-435 cells with differing concentrations of a cell medium extract of *Glinus lotoides* (MsWM-CAMY-3T).

Cytotoxicity was also evaluated by DYNE MRX. To accomplish this, 20 μls of Almarblue was added to each well of the test plate, incubating at 37° C. for at least four hours, and reading the oxidation levels by DYNE MAX. The graph in FIG. 20 displays the results of this experiment. The cytotoxic effect increased with the increase in concentration of MsWM-CAMY3T tested. The lowest cell densities were obtained at concentrations of 0.00160% and above.

These results indicate the efficacy of cancer cell treatment with extracts of *Hagenia abyssinica* (CAM-MsWM); *Millettia ferruginea* (CAM-YING); *Ruta chalepensis* (CAM-ANQZ), and *Glinus iotoide* (MsWM-CAMY3T).

The invention has been described by reference to its specific embodiments. Those of skill in the art will recognize that the invention should not be so limited.

What is claimed is:

1. A method for preparing a composition comprising an extract of a plant material selected from the group consisting of *Millettia ferruginea*, and mixtures of *Millettia ferruginea* with at least one or more extracts from a plant material selected from the group consisting of *Glinus lotoids, Ruta chalepensis, Hagenia abyssinica*, comprising:
    (a) contacting the plant material with a solvent selected from the group consisting of hexane, ether, and acetone, or mixture of solvents selected from the group consisting of methanol, hexane, ether, and acetone, to form a liquid extract and a crude material, and
    (b) separating the liquid extract compositions from the crude material.

2. The method of claim 1, wherein the solvent or mixture of solvents is polar.

3. The method of claim 1, wherein the solvent or mixture of solvents is non-polar.

4. The method of claim 1, wherein the solvent is selected from the group consisting of methanol, hexane, ether, and acetone.

5. The method of claim 1, wherein the plant material is selected from the group consisting of flowers, leaves, seeds, stems, and, mixtures thereof.

6. The method of claim 1, wherein the composition comprises two or more extracts of plant material derived from the same or different plants.

7. The method of claim 1, wherein separating (b) comprises a method selected from the group consisting of centrifugation, filtration, and allowing the mixture to settle.

8. The method of claim 1, wherein separating (b) comprises multiple centrifugations resulting in the recovery of multiple liquid extracts.

9. The method of claim 8, wherein the multiple liquid extracts are combined.

10. The method of claim 1, further comprising:
    (c) contacting the crude material one or more times with the same or different solvent selected from the group consisting of hexane, ether, and acetone, or mixture of solvents selected from the group consisting of hexane, ether, acetone and methanol to form one or more additional liquid extracts and one or more additional crude materials, and
    (d) separating the one or more additional liquid extracts from the one or more additional crude materials.

11. The method of claim 10, further comprising:
    (i) optionally combining one or more of the one or more liquid extracts;

(ii) removing the solvent selected from the group consisting of hexane, ether, and acetone, or mixture of solvents from the one or more liquid extracts to produce a substantially dried pellet, and (iii) suspending the substantially dried pellet in an aqueous solution.

12. The method of claim 1, further comprising combining the liquid extract with a suitable pharmaceutical carrier.

13. The method of claim 1, further comprising process step (b) removing the mixture of solvents selected from the group consisting of methanol, hexane, ether, and acetone from the liquid extract to produce a substantially died pellet, and combining the substantially dried pellet with a suitable pharmaceutical carrier.

14. The method of claim 12, wherein the pharmaceutical carrier is suitable for administration by a method selected from the group consisting of oral administration, intranasal administration, rectal administration, and parenteral administration.

15. The method of claim 14, wherein the parenteral administration is intravenous, ubcutaneous, intramuscular, or intraperitoneal injection.

16. The method of claim 12, wherein the pharmaceutical carrier is in a form selected from the group consisting of tablets, capsules, powders, suppositories, suspensions, and solutions.

17. The method of claim 12, wherein the pharmaceutical carrier comprises coloring agents, flavoring agents, or combinations thereof.

18. A method for preparing a composition comprising one or more extracts of plant material, wherein the extract is obtained from a plant material selected from the group consisting of (1) *Millettia ferruginea* or (2) a mixture of *Millettia ferruginea* with a plant material consisting of *Glinus lotoides, Ruta chalepensis*, and *Hagenia abyssinica*, comprising:

(a) contacting the plant material with a solvent selected from the group consisting of hexane, ether, and acetone, or mixture of solvents selected from the group consisting of methanol, hexane, ether, and acetone to form a liquid extract and the crude material;

(b) separating the liquid extract and the crude material; and (c) optionally contacting the crude material one or more times with the same or different solvent or mixture of solvents selected from the group consisting of methanol, hexane, ether, and acetone to form one or more additional crude materials and one or more additional liquid extracts, wherein at least one of the contacting steps (a) or (c) comprises adjusting the pH by adding a basic compound or an acidic compound to form an adjusted mixture.

19. The method of claim 18, wherein the pH is adjusted by adding a basic compound.

20. The method of claim 19, wherein the basic compound is NaOH.

21. The method of claim 19, wherein the pH is adjusted to a value between about 9 to about 13.

22. The method of claim 18, wherein the pH is adjusted by adding an acidic compound.

23. The method of claim 22, wherein the acidic compound is HCI.

24. The method of claim 22, wherein the pH is adjusted to a value from about 1 to about 5.

25. The method of claim 18, further comprising re-adjusting the pH of the adjusted mixture, comprising:

(i) adding an acidic compound if a basic compound was added, or (ii) adding a basic compound if an acidic compound wan added.

26. The method of claim 18, further comprising:

(d) optionally combining one or more of the one or more liquid extracts;

(e) adjusting the pH to about 6 to about 8; and (f) mixing the one or more liquid extracts with a suitable pharmaceutical carrier.

27. The method of claim 18, further comprising repeating (a)–(c) using a different plant material for the mixture with *Millettia ferruginea* and the same or different solvent or a mixture of solvents selected from the group consisting of methanol, hexane, ether, and acetone.

28. A method for preparing a composition comprising one or more extracts of plant material, wherein the plant material is obtained from a plant selected from the group consisting of (1) *Millettia ferruginea* or (2) a mixture of *Millettia ferruginea* with at least one plant material selected from the group consisting of *Glinus lotoides, Ruta chalepensis*, and *Hagenia abyssinica*. comprising:

(a) contacting the plant material with a solvent selected from the group consisting of hexane, ether, and acetone, or mixture of solvents selected from the group consisting of methanol, hexane, ether, and acetone to form a first liquid extract and a first crude material;

(b) separating the first liquid extract from the first crude material;

(c) contacting the first crude material with the same or a different solvents or a mixture of solvents selected from the group consisting of hexane, ether, acetone and methanol comprising a second liquid extract and a second crude material;

(d) adjusting pH of the mixture (c) by adding a basic compound;

(e) separating the second liquid extract from the second crude material;

(f) contacting the second crude material with the same or a different solvents or a mixture of solvents selected from the group consisting of hexane, ether, acetone and methanol to form a mixture comprising a third liquid extract and a third crude material;

(g) adjusting the pH of the mixture (f) by adding an acidic compound; and (h) separating the third liquid extract from the third crude material.

29. The method of claim 28, further comprising:

(i) optionally performing additional contacting, adjusting, or separating steps;

(ii) combining one or more of the liquid extracts;

(iii) adjusting the pH to about 6 to about 8; and (iv) mixing the one or more liquid extracts with a suitable pharmaceutical carrier.

30. A composition obtained by the method of claim 28.

31. A composition obtained by the method of claim 29.

32. A method of treating breast cancer, prostate cancer, leukemia, melanoma, myeloma, HIV and other viral infection, diabetes, Parkinson's disease, tuberculosis, or fungal infections comprising administration of a therapeutic amount of one or more extracts of plant material from composition of claim 12.

33. A method of treating breast cancer, prostate cancer, leukemia, melanoma, myeloma, HIV and other viral infection, diabetes, Parkinson's disease, tuberculosis, or fungal infections comprising administration of a therapeutic amount of one or more extracts of plant material from composition of claim 13.

34. A pharmaceutical composition obtained by method 28.

35. A pharmaceutical composition obtained by method 29.

36. The method of claim 32, wherein the cancer is selected from the group breast cancer, leukemia, melanoma, and myeloma.

37. The method of claim 33, wherein the cancer is selected from the group breast cancer, leukemia, melanoma, and myeloma.

38. The method of claim 32, wherein the composition is administered by a method selected from the group consisting of oral administration, intranasal administration, rectal administration, and parenteral administration.

39. The method of claim 33, wherein the composition is administered by a method selected from the group consisting of oral administration, intranasal administration, rectal administration, and parenteral administration.

40. The method of claim 38, wherein *Millettia ferruginea* is administered orally at a daily dosage level ranging from about 10 mg/kg to about 100 mg/kg body weight of the patient.

41. The method of claim 39, wherein *Millettia ferruginea* is administered orally at a daily dosage level ranging from about 10 mg/kg to about 100 mg/kg body weight of the patient.

* * * * *